United States Patent
Begue et al.

(10) Patent No.: US 10,454,034 B2
(45) Date of Patent: Oct. 22, 2019

(54) HEXABENZOCORONENE-BASED COMPOUND FOR ORGANIC PHOTOVOLTAIC CELLS

(71) Applicants: Centre National De La Recherche Scientifique, Paris (FR); Universite De Pau Et Des Pays De L'Adour, Pau (FR)

(72) Inventors: Didier Begue, Serres Morlaàs (FR); Roger Clive Hiorns, Arudy (FR); Hugo Santos-Silva, Pau (FR); Emilie Guille, Angais (FR); Charlène Boussiron, Pau (FR); Christine Dagron-Lartigau, Billere (FR); Pierre Iratcabal, Pau (FR)

(73) Assignees: CENTRE NATIONAL DE LA RECHERCHE SCIENTIFIQUE, Paris (FR); UNIVERSITE DE PAU ET DES PAYS DE L'ADOUR, Pau (FR)

( * ) Notice: Subject to any disclaimer, the term of this patent is extended or adjusted under 35 U.S.C. 154(b) by 109 days.

(21) Appl. No.: 15/556,053

(22) PCT Filed: Mar. 11, 2016

(86) PCT No.: PCT/IB2016/051411
§ 371 (c)(1),
(2) Date: Sep. 6, 2017

(87) PCT Pub. No.: WO2016/142923
PCT Pub. Date: Sep. 15, 2016

(65) Prior Publication Data
US 2018/0047906 A1 Feb. 15, 2018

(30) Foreign Application Priority Data

Mar. 12, 2015 (WO) .................. PCT/IB2015/000511

(51) Int. Cl.
*C08L 65/00* (2006.01)
*H01L 51/00* (2006.01)
(Continued)

(52) U.S. Cl.
CPC ........ *H01L 51/0036* (2013.01); *C07D 333/06* (2013.01); *C08G 61/126* (2013.01);
(Continued)

(58) Field of Classification Search
CPC .............. C08G 61/126; H01L 51/0056; H01L 51/0036
See application file for complete search history.

(56) References Cited

U.S. PATENT DOCUMENTS

2008/0035915 A1* 2/2008 Russell ............... H01L 51/0004
257/40
2012/0024382 A1* 2/2012 Holmes ................. C07C 13/567
136/263

OTHER PUBLICATIONS

Wong, Chem. Mater., 2010, 22 (2), pp. 457-466 (Year: 2010).*
(Continued)

*Primary Examiner* — Robert C Boyle
(74) *Attorney, Agent, or Firm* — Alston & Bird LLP

(57) ABSTRACT

Provided is a hexabenzocoronene-based compound and a donor: acceptor layer having this compound. Also provided are processes for manufacturing this compound and to a photovoltaic cell having at least one hexabenzocoronene-based compound. The hexabenzocoronene-based compound has following formula I:

(Continued)

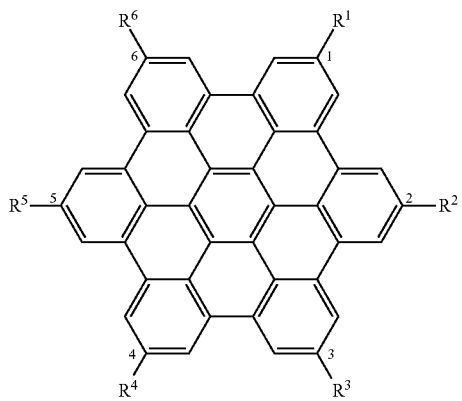

wherein $R^1$, $R^3$, $R^4$ and $R^6$ are independently from each other chosen among a carboxylic (—COOH) group, a cyano (—C≡N) group, an isocyano (—N$^+$≡C$^-$) group, a cyanate (—O—C≡N) group and a —F group, and $R^2$ and $R^5$ are, independently from each other, chosen among a poly(3-oxypentylthiophene) (P3OPT) substituent and a poly(3-hexylthiophene) (P3HT) substituent.

21 Claims, 4 Drawing Sheets

(51) Int. Cl.
  *C08G 61/12* (2006.01)
  *C07D 333/06* (2006.01)
  *H01L 51/42* (2006.01)

(52) U.S. Cl.
  CPC .......... *C08L 65/00* (2013.01); *H01L 51/0056* (2013.01); *H01L 51/4253* (2013.01); *C08G 2261/1412* (2013.01); *C08G 2261/1424* (2013.01); *C08G 2261/3223* (2013.01); *C08G 2261/91* (2013.01); *Y02E 10/549* (2013.01)

(56) References Cited

OTHER PUBLICATIONS

Jones, Chem. Commun., 2012, 48, p. 8066-8068 (Year: 2012).*
Thompson, Macromolecules 2014, 47, p. 8645-8652 (Year: 2014).*
Gupta, V. et al., *Luminscent Graphene Quantum Dots for Organic Photovoltaic Devices*, Journal of the American Chemical Society, vol. 133 (2011) 9960-9963.
Hesse, H. C. et al., *Large polycyclic aromatic hydrocarbons for application donor-acceptor photovoltaics*, Phys. Status Solidi, vol. 209, No. 4 (2012) in 785-789.
International Search Report and Written Opinion for corresponding International Application No. PCT/IB2015/000511, dated Aug. 7, 2015.
International Search Report and Written Opinion for corresponding International Application No. PCT/IB2016/051411, dated May 23, 2016.
Jones, D. J. et al., *Synthesis of electron-poor-hexa-perihexabenzocoronenes*, Chem. Commun, vol. 48 (May 2012) 8066-8068.
Sonar, P. et al., *Organic non-fullerence acceptors for organic photovoltaics*, Energy Environ. Sci., vol. 4 (2011) 1558-1574.
Thompson, C. M. et al., *Substituent Effects on the Gas Sorption and Selectivity Properties of Hexaphenylbenzene and Hexabenzocoronene Based Porous Polymers*, Macromolecules, vol. 47 (2014) 8645-8652.
L. Schmidt-Mende et al. in, Science 111, 293, 2001.
Mackie et al (J. Phys. Chem. A 2008, 112, 10968).
B. Park et al., Synth, Met. 1993, 56, 3258).
B.R. Brooks et al., J. Comp. Chem, 2009, 30, 1545.
D. Andrienko et al., J. Chem. Phys. 2006 125, 124902.
J. Liu, R. S. Loewe, R. D. McCullough, Macromolecules 1999, 32, 5777.
A. Fechtenkotter, N. Tchebotarva, M. Watson, K. Mullen Tetrahedron, 2001, 57(17), 3769-3783.
X. Yang, X. Dou, A. Touhanipour, L. Zhi, H. J. Rader, K. Mullen, J. Am. Chem Soc., 2008, 130, 4216-4217.
L. Zhai, R. Shukla, R. Rathore, Org. Lett. 2009, 11, 3474-3477.
G. E. Morse, A. Tournebize, A. Rivation. T. Chasse, C. Taviot-Gueho, Phys. Chem Chem. Phys. 2015, 17, 11884.
Wheeler, Steven E., *Controlling the local arrangements of [pi]-stacked polycyclic aromatic hydrocarbons through substituent effects*, Crystengcomm, vol. 14, No. 19 (2012) 6140-6145.
Wong, W. W. et al., *Synthesis, Photophysical, and Device Properties of Novel Dendrimers Based on a Fluorene—Hexabenzocoronene (FHBC) Core*, Organic Letters, vol. 11, No. 4 (2009) 975-978.

* cited by examiner

HEXABENZOCORONENE-BASED COMPOUND FOR ORGANIC PHOTOVOLTAIC CELLS

FIELD

The invention relates to a hexabenzocoronene-based compound, to a donor: acceptor layer comprising this compound. The invention also relates to processes for manufacturing these compounds and to a photovoltaic cell comprising at least one hexabenzocoronene-based compound of the invention.

BACKGROUND

The search for new donor: acceptor pairs for organic photovoltaic (OPV) applications is highly important for socio-economic and environmental reasons.

From the point of view of performance and stability, the composite couple of poly(3-hexylthiophene):[6,6]-phenyl-$C_{61}$-methyl butyrate (P3HT:PCBM) has long been the standard bearer.

However, the poor electronic correlation between the donor (P3HT) and the acceptor (PCBM), combined with numerous morphological instabilities at the heart of the heterojunction are two of the major problems that are tackled through diverse solutions proposed in the literature.

The search for a better correlation in the electronic properties ranges from minor modifications in the chemical structures of one of the pair components to complete replacement of the donor or acceptor molecule.

Due to the inherent difficulties of synthesising or grafting groups onto fullerene, the precursor of PCBM, numerous authors have sought to replace it.

Accordingly, graphene-based materials have rapidly appeared as good acceptor candidates, primarily because of their remarkable semiconducting properties.

In particular, Jones et al. in "Synthesis of electron-poor-hexa-peri-hexabenzocoronenes", Chem. Commun, 2012, 48, 8066-8068, disclose a series of hexabenzocoronene (HBC) derivatives containing Br, F, CF3 and aryl substituents said to be appropriate acceptors to be substituted to PCBM in the composite couple of P3HT:PCBM.

However, the short current circuit $J_{sc}$ of this composite couple is quasi-null so that the efficacy of the OPV devices using this composite couple is also quasi-null. The efficacy depends from the product ($V_{oc} \times J_{sc} \times FF$) divided by the power in, where FF is the fill factor and the $V_{oc}$ is the open circuit Voltage. The FF is the product of the maxima of the voltage and current divided by the product of the $V_{oc}$ and the $J_{sc}$. Furthermore the donor and acceptor are a blend and are not covalently connected, therefore the charge transfer is hindered by this nanoscale disorganisation.

Also, L. Schmidt-Mende et al. in, Science 111, 293, 2001, describe columnar systems in which the donor is an HBC modified by alkyl chains and the acceptor is a alkyl modified perylene and in which all other substituents are H, such an HBC. However, the electronic levels of the HBC moieties have not been modified through careful change of substituent groups to optimize the electronic efficacy nor have the donor and acceptor been covalently linked to provide structural stability and self-organization to optimize charge-collation and transfer to electrodes.

But, materials in organic photovoltaic cells should ideally be adapted and optimized for maximum efficiency at each stage of the process of converting solar energy into electricity.

SUMMARY

In this context, the invention aims to propose materials for organic photovoltaic applications based on graphene enabling to obtain such a maximum efficiency.

For attaining this aim, the invention proposes a hexabenzocoronene-based compound of following formula I:

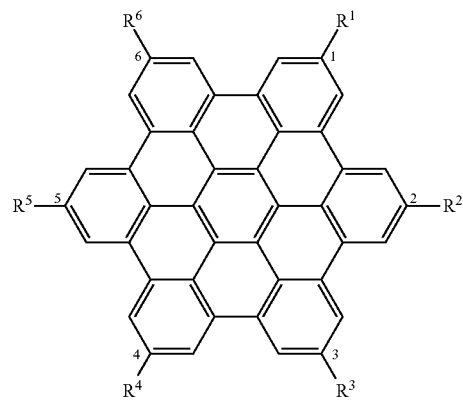

wherein $R^1$, $R^3$, $R^4$ and $R^6$ are independently from each other chosen among a carboxylic (—COOH) group, a cyano (—C≡N) group, an isocyano (—N$^+$≡C$^-$) group, a cyanate (—O—C≡N) group and a —F atom, and $R^2$ and $R^5$ are, independently from each other, chosen among a poly(3-oxypentylthiophene) (P3OPT) substituent and a poly(3-hexylthiophene) (P3HT) substituent.

Preferably in the hexabenzocoronene-based compound of the invention, $R^1$, $R^3$, $R^4$ and $R^6$ are identical.

Still preferably in the hexabenzocoronene-based compound of the invention, $R^2$ and $R^5$ are identical and are a poly(3-oxypentylthiophene) substituent.

Again preferably in the hexabenzocoronene-based compound of the invention, $R^1$, $R^3$, $R^4$ and $R^6$ are identical and are carboxylic groups.

The invention also proposes a donor: acceptor layer comprising a stack of hexabenzocoronene-based compound according to the invention.

A device comprising at least one hexabenzocoronene-based compound according to the invention is also proposed by the invention.

Preferably, this device is a photovoltaic cell.

BRIEF DESCRIPTION OF THE DRAWINGS

The invention will be better understood and other advantages and characteristics thereof will appear more clearly when reading the following description which is made in reference to the figures in which.

DETAILED DESCRIPTION

Figure 1:
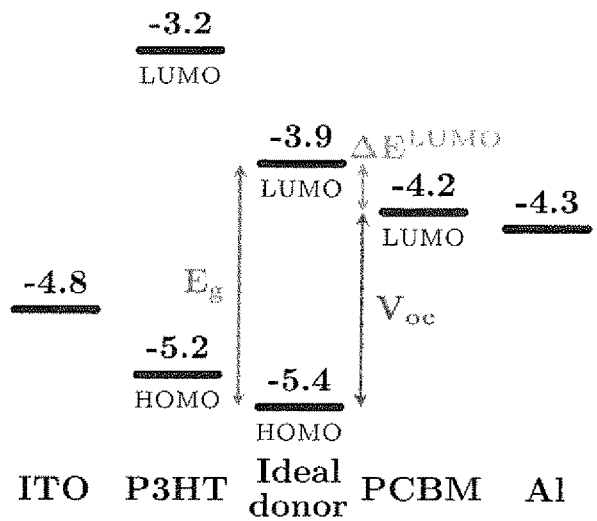
FIG. 1 shows the band-structure of the donor: acceptor P3HT:PCBM compared to that of an ideal donor: acceptor pair.

Based on a comparison between the band-structure of P3HT:PCBM and that of an ideal donor: acceptor pair, schematically represented in FIG. 1, the key parameters to be optimized for obtaining a material adapted and optimized for maximum efficiency of an organic photovoltaic cell at each stage of the process for converting solar energy into electricity are briefly summarized as being:

i) the energy difference between the LUMO of the donor and the LUMO of the acceptor ($\Delta E^{LUMO}$), which should be of the order of 0.3 eV to ensure ideal efficiencies during exciton transfer. This value is sufficient to provoke ultra-fast electron transfer from the donor to the acceptor and cannot be reduced due to the possibility of charge transfer reversal.

ii) the bandgap ($E_g$) of the donor molecule which should be close to 1.5 eV. For P3HT this value is about 1.9 eV and therefore too high, thus limiting the absorption of light in the infrared range by the polymer.

iii) the open circuit voltage ($V_{oc}$) must be adjusted: if it is too high, a large amount of the energy is lost. If it is too low, the resulting OPV would work at an unnecessary low voltage, making the potential energy conversion inefficient.

The inventors have now discovered that new graphene-based materials, namely hexabenzocoronene (HBCs), meet the requirements of the whole set of parameters that govern the efficiency of the organic photovoltaic (OPV) device from both electronic and oxidative stability points of view.

More precisely, hexabenzocoronene-based compound (HBC) having the formula I below:

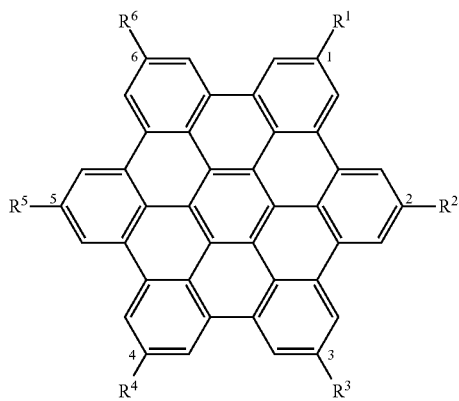

wherein $R^1$, $R^3$, $R^4$ and $R^6$ are independently from each other chosen among a carboxylic (—COOH) group, a cyano (—C≡N) group, an isocyano (—N⁺≡C⁻) group, a cyanate (—O—C≡N) group and a —F group, and $R^2$ and $R^5$ are, independently from each other, chosen among a poly(3-oxypentylthiophene) (P3OPT) substituent and a poly(3-hexylthiophene) (P3HT) substituent, were proven to have the expected electronic properties.

They are superior to PCBM by way of their two-dimensionality, they avoid micro aggregations resulting in a disruption of the morphology and a rupture of the active layer and the device, they increase exciton pathway lengths and facilitate charge transport.

This is due to the columnar structure of these compounds which provides a channel for the electron flux and thus enables charges to diffuse to the electrode through a favourable graphene/electrode interaction.

The columnar structure is obtained by the choice of the position and nature of the substituents $R^1$, $R^3$, $R^4$ and $R^6$ in formula I. Such a choice permits to obtain an optimal close stacking of the different layers of the HBC of the invention.

This columnar structure is very stable due to the choice of the substituents $R^1$, $R^3$, $R^4$ and $R^6$.

Furthermore, all these substituents permit to fit the electronic levels of graphene of the HBC core so that these levels are in optimal phase for the electronic transfer from the donor system to the acceptor system.

Among the substituents which are chosen among a carboxylic group, a cyano group, an isocyano group, a cyanate group and a —F group, for $R^1$, $R^3$, $R^4$ and $R^6$ a carboxylic group is particularly preferred because it is easier to graft on the HBC core.

In the compound of the invention, the positions 2 and 5 are occupied with a conductor polymer which is, in the invention, chosen among a poly(3-oxypentylthiophene) (P3OPT) and a poly(3-hexylthiophene) (P3HT) substituent. Thus $R^2$ and $R^5$ in formula I may be both a P3OPT or a P3HT or one of $R^2$ and $R^5$ is P3OPT and the other is P3HT.

However, preferably $R^2$ and $R^5$ are identical.

In the preferred compound of the invention of formula I, $R^1$, $R^3$, $R^4$ and $R^6$ are identical and are a carboxylic group and $R^2$ and $R^5$ are also identical and are P3OPT substituents because when different layers of these compounds are formed, they are perfectly stacked.

Figure 3:
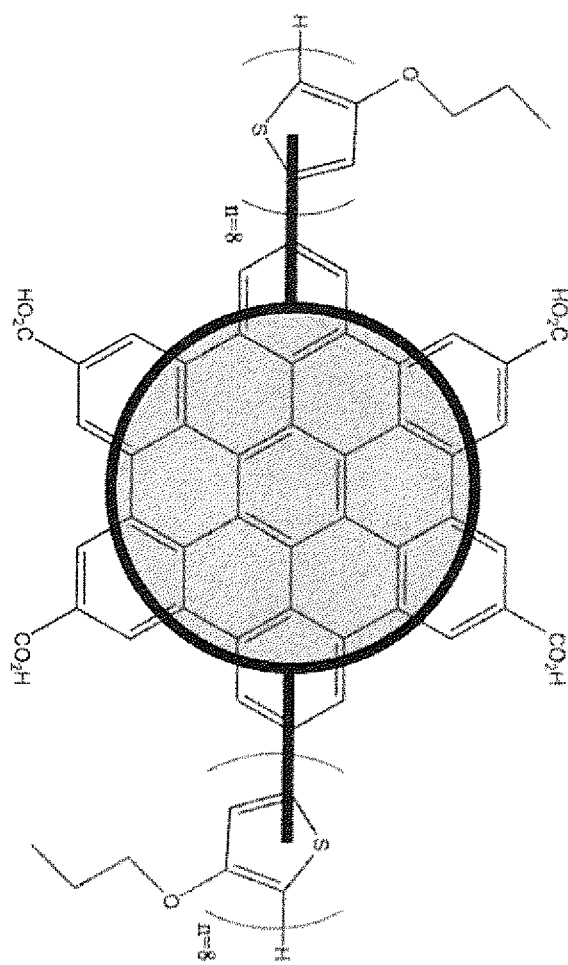

The compound of the invention has the structure shown in FIG. 3.

Figure 4:
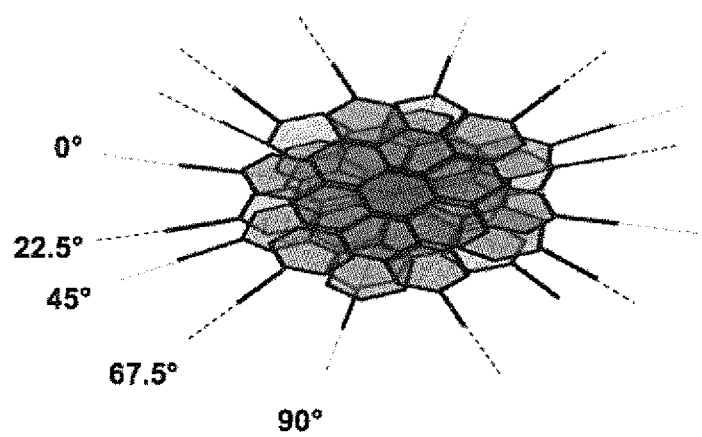
Figure 5:
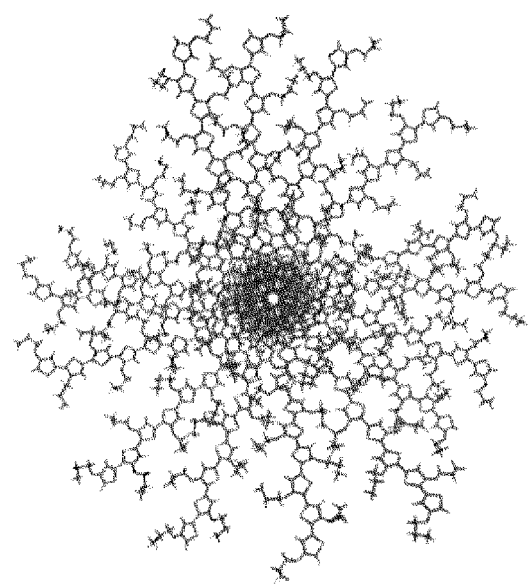

When stacked, the different layers formed of the compound of formula I are stacked as shown in FIG. 4 at the beginning of the stacking and as shown in FIG. 5 at the end of this stacking.

Figure 7:
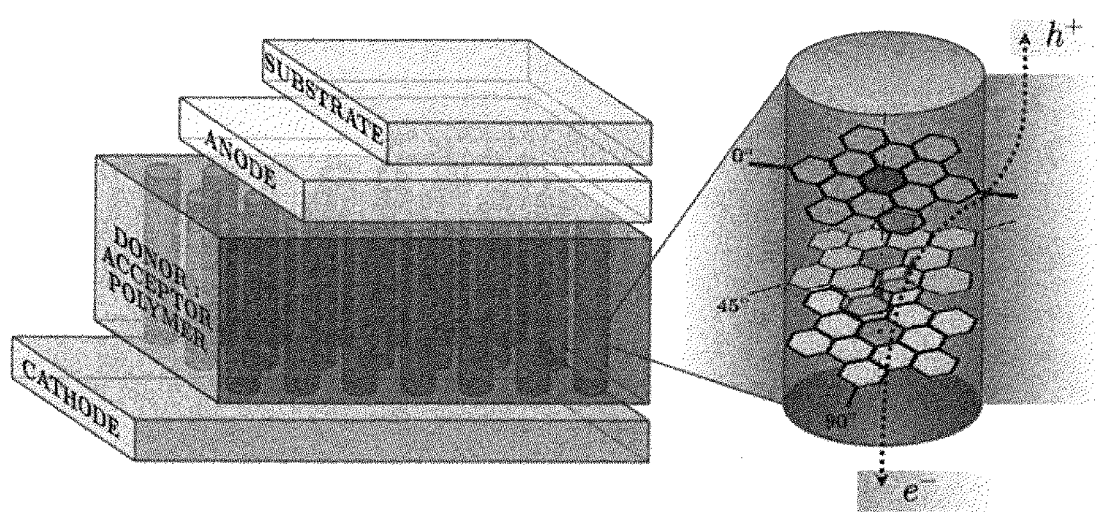

As one can see from FIGS. 3 and 4, the compound of the invention forms a compact stack while providing a columnar structure as shown on the right on of FIG. 7.

Thus, by appropriate chemical functionalization of circular hexabenzocoronenes (circ-HBCs) the inventors have found an acceptor compound with electronic properties that match the donor compound, in the present case P3OPT or P3HT or a mixture thereof.

The substituents used for this chemical functionalization, which are to be grafted on positions 1, 3, 4 and 6 of the HBC core, are independently from each other chosen among a carboxylic (—COOH), cyano (—C≡N), isocyano (—N⁺≡C⁻), cyanate (—O—C≡N) and —F group.

Preferably, the substituent $R^1$, $R^3$, $R^4$ and $R^6$ are identical and more preferably, they are a carboxylic group.

The substituents $R^1$, $R^3$, $R^4$ and $R^6$ modulate the electronic position of the LUMO's acceptor according to the electronic HOMO-LUMO electronic position of the selected donor.

Moreover, their steric effect enables to obtain a columnar structure which channel the electron flux and thus enable charges to diffuse to the electrode.

The HOMO and LUMO energy of the two donor systems (P3HT and P3OPT) with an acceptor according to the invention which is an HBC of formula I in which $R^1$, $R^3$, $R^4$ and $R^6$ are identical and are either an hexyl, $CO_2H$, —$CO_2C_4H_9$ and —$CO_2C_6H_{13}$ are given in following table 1.

Also, for comparison, the HOMO and LUMO energy of the same donor systems with an acceptor which is also an HBC but not according to the invention are given in following table 1. These HBC based-compounds are triangular HBCs.

TABLE 1

Calculated $\Delta E^{LUMO}$ and $V_{oc}$ (eV) values of the graphene-based molecules relative to that of P3HT and P3OPT donors.

| acceptor: | R = | $\Delta E^{LUMO}$ (eV) vs. donor P3HT | $\Delta E^{LUMO}$ (eV) vs. donor P3OPT | $V_{oc}$ (eV) vs. donor P3HT | $V_{oc}$ (eV) vs. donor P3OPT |
|---|---|---|---|---|---|
| [triangular graphene structure] | H | −0.15 | −0.38 | 2.15 | 1.79 |
| | hexyl | −0.26 | −0.49 | 2.26 | 1.90 |
| | $CO_2H$ | 0.18 | −0.05 | 1.82 | 1.46 |
| | $CO_2C_4H_9$ | −0.03 | −0.26 | 2.03 | 1.67 |
| | $CO_2C_6H_{13}$ | −0.03 | −0.26 | 2.03 | 1.67 |
| [circ-HBC structure] | H | −0.35 | −0.58 | 2.35 | 1.99 |
| | hexyl | −0.45 | −0.68 | 2.45 | 2.09 |
| | $CO_2H$ | 0.55 | 0.32 | 1.45 | 1.09 |
| | $CO_2C_4H_9$ | 0.24 | 0.01 | 1.76 | 1.40 |
| | $CO_2C_6H_{13}$ | 0.23 | 0.00 | 1.75 | 1.39 |
| PCBM | | 1.00 | 0.77 | 1.00 | 0.64 |
| Ideal P3HT:PCBM | | | | 0.3 | 1.3 |

Figure 2:
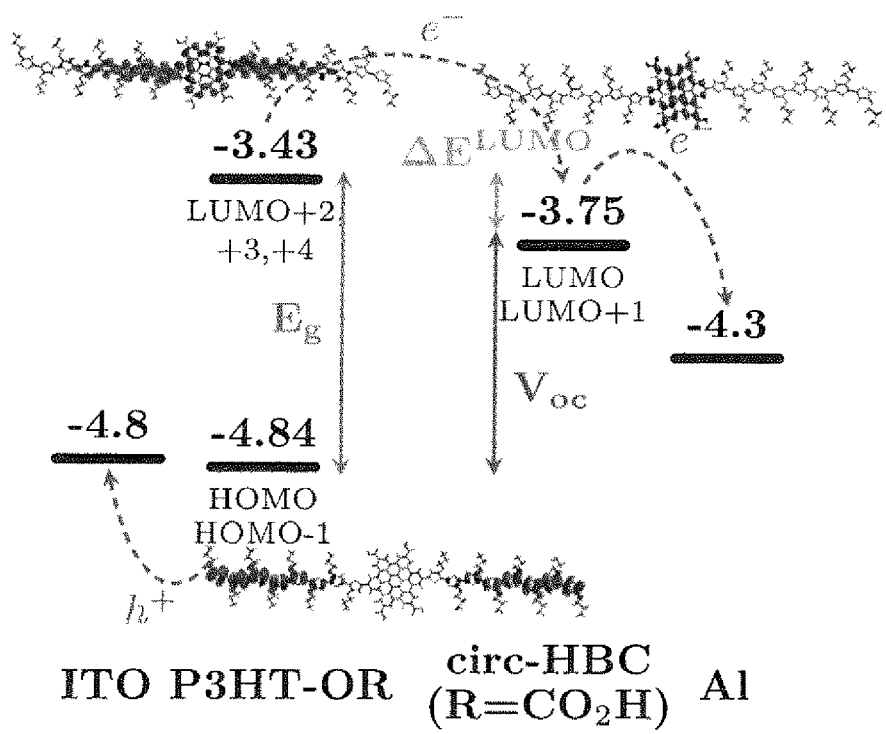
FIG. 2 shows the band-structure of a donor: acceptor pair which is a compound of the invention compared to that of the donor: acceptor P3HT:PCBM, FIG. 3 schematically shows the molecule structure of a compound of the invention, FIG. 4 schematically represents the stacking pattern at the start of the stacked molecules of the invention, FIG. 5 schematically represents a top view on the stacked molecules of the invention.

These HOMO and LUMO energy are also given in FIGS. 1 and 2.

In FIG. 1, the donor systems P3HT and PCBM are compared to the ideal donor and in FIG. 2, the donor system comprising a circ-HBC in which the substituents $R^1$, $R^3$, $R^4$ and $R^6$ are identical and are carboxylic groups, are compared to that of the donor system P3HT-OR in which R is also a carboxylic group.

In this donor system, P3OPT is used as it has already showed a reduced intrinsic bandgap of 1.4 eV, making it possible to attain the theoretically optimised value of 1.5 eV, and is expected to demonstrate high stability and photostability.

In addition, P3OPT gives rise to a greater electronic delocalisation which can favour the transfer of charges between the donor and the acceptor.

The chosen acceptor, i.e. the two-dimensional HBC, also shows a greater electronic delocalisation than that of PCBM due to the greater accessibility of the involved π-orbitals. As a consequence, the global delocalisation of electrons over the whole donor:acceptor system favours the transfer of charges.

The electronic levels of grafted circ-HBC molecules which are compounds of the invention, are in good agreement with, both an 'ideal electronic situation' (FIG. 1), the experimental attempt and the data reported by Gupta et al. into "Graphene Quantum Dots" *J. Am Chem. Soc.*, 2011, 133, 9960. Interestingly, the theoretical data gathered on HBC systems demonstrate that the shape and functionalization of these molecules lead to a wealth of possibilities to modulate the electronic properties on a wide energy range. Both triangular and circular functionalized HBCs could get close to the ideal configuration (regarding $V_{oc}$ and $\Delta E^{LUMO}$) to match the target donor material P3OPT. However, it is clear that circ-HBC, allows much greater modularity when grafted by electron-withdrawing substituents. The systems constituted of a circ-HBC grafted with a $CO_2H$ substituent combined with P3OPT as donor material was calculated to possess a $\Delta E^{LUMO}$ of 0.32 eV and an open-circuit voltage of 1.09 eV. These two values, jointly to the Density Functional Theory (DFT) calculated HOMO/LUMO orbitals of the single P3OPT-circ-HBC(R—$CO_2H$)—P3OPT of the invention depicted in FIG. 3 get very close to an ideal OPV system and provide an extremely good test candidate for future studies.

The intrinsic ability of the compound of the invention to form ordered stacks—the structure of which depends on the type of HBC substituents—is a useful property in that charge maybe more easily transponed to the electrodes.

Additional investigations on the π-stacking properties using ab initio, DFT and molecular dynamics (MD) simulations were carried out. While using graphene-based acceptor molecules for the ab initio and DFT simulations, molecular dynamic simulations were applied to the combined donor:acceptor molecule of the invention (P3OPT—circ-HBC(R=$CO_2H$)—P3OPT, see FIGS. 4 and 5, to investigate the stability of these π-stacked arrangements of HBC molecules of the invention in solution with an organic solvent.

An evaluation of the geometrical and electronic properties was performed and compared with graphite itself. The inter-HBC equilibrium distances was calculated to be 3.43 and 3.47 at ωB97XD/6-31G* and SAPT-DFT [PBE0/cc-pVDZ] levels of calculation respectively. These results compare favourably to the inter-sheet distance of graphite (3.35) and also to the results reported by Mackie et al (*J. Phys. Chem. A* 2008, 112, 10968 and references therein) using various levels of theory. Further performance enhancements for OPVs are expected to be possible from directly linking donor and acceptor in a single molecule due to improved electron transfer rates. To ensure already at an early stage that the changes to the HBC core does not in principle infringe the π-stacking, the behaviour of functionalized circ-HBC in solution was dynamically-simulated.

FIG. 4 shows the π-stacking of the functionalized circ-HBC of the invention at the start and FIG. 5 shows this π-stacking at the end of.

After equilibrating the system for 1 ns (releasing more and more parts of the systems), a convergence via energy and structural features is obtained.

For the production run of 2.5 ns, an average distance of 3.45 between two circ-HBC molecules of the invention is obtained, which is in very good agreement with experimental (B. Park et al., *Synth. Met.* 1993, 56, 3258) and theoretical (B. R. Brooks et al., *J. Comp. Chem.* 2009, 30, 1545, and D.

Figure 6:
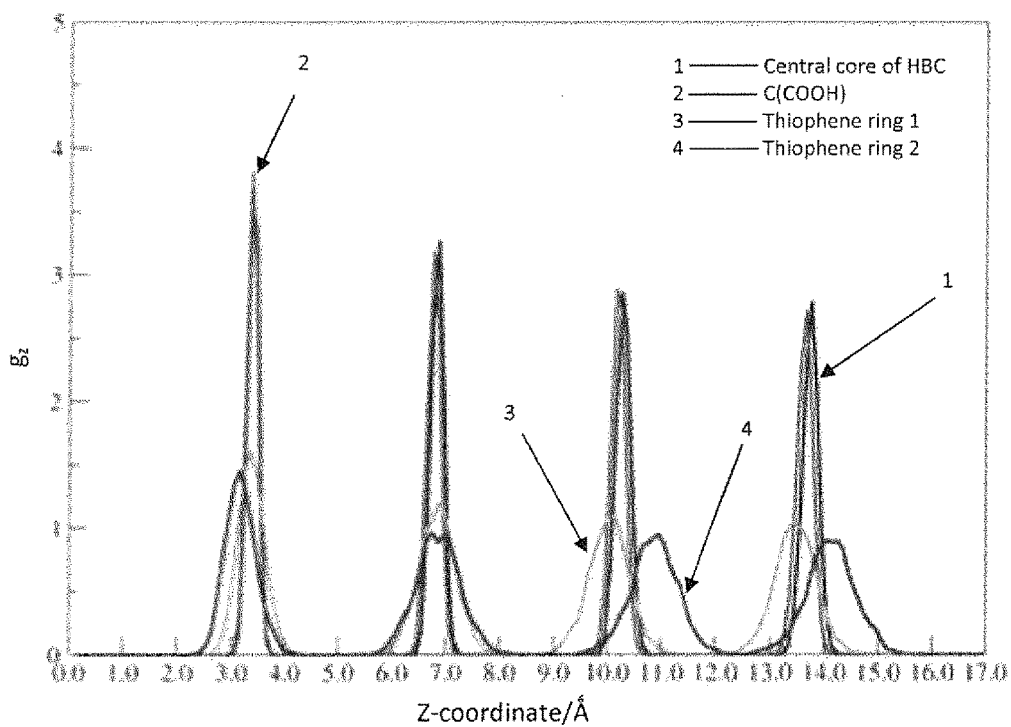
FIG. 6 is a curve showing the stacking pattern of the molecules of the invention, FIG. 7 schematically represents a device comprising a stacking of compounds of the invention forming a donor: acceptor layer located between an anode and a cathode.

Andrienko et al., *J. Chem. Phys.* 2006 125, 124902) results for similar systems. The π-stacked structure remains stable throughout the whole simulation time and the stacking of the molecules is illustrated in FIGS. 4, 5 and FIG. 6. FIG. 6 provides the distribution function $g_z$, in dependency of the z-coordinate.

The HBC based-compound of the invention was demonstrated to be a suitable model of graphene, its size and structure being well adapted to replace PCBM because of its two-dimensionality. In addition to its electronic properties, its columnar structure (which should resolve the weak efficiency observed by Gupta et al. with Graphene Quantum Dots) channels the electron flux and thus enable charges to diffuse to the electrode through a favorable graphene/electrode interaction. The influence of the substitution by side chains on the energy of the LUMO level of HBC provided exactly what the inventors were hoping to achieve: for a two component system consisting of a circ-HBC grafted with a —$CO_2H$ substituent as acceptor and P3OPT as donor, the obtained $\Delta E^{LUMO}$=0.32 and $V_{oc}$=1.09 eV, both excellent values to form a highly efficient solar cell.

Thus, the compound of formula I of the invention has been proved to be quite appropriate for forming the donor: acceptor layer.

FIG. 7 schematically shows such a donor: acceptor layer located between the two electrodes.

Accordingly, a donor: acceptor layer comprising at least one compound of formula I of the invention is also a subject matter of the invention as well as any device comprising at least one compound of formula I of the invention.

More particularly, this device is an organic photovoltaic cell.

A compound of formula I which is particularly preferred in the invention is the compound of the following formula I-1:

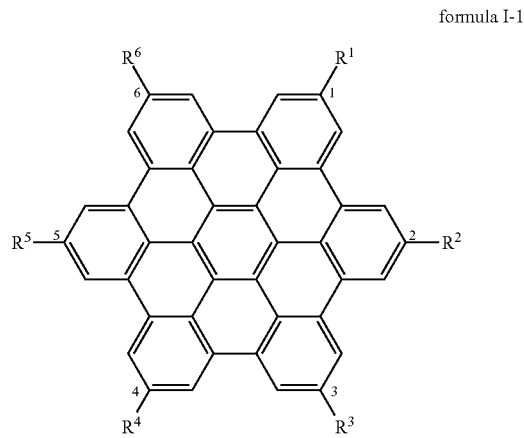

formula I-1 wherein $R^1$, $R^3$, $R^4$ and $R^6$ are identical and are a carboxylic group (—COOH), and $R^2$ and $R^5$ are identical and are chosen among a poly(3-oxypentylthiophene) (P3OPT) substituent and a poly(3-hexylthiophene) (P3HT) substituent.

The invention proposes three methods of synthesis of this compound of formula I-1.

The schema reaction of the first method of synthesis of the invention is as follows:

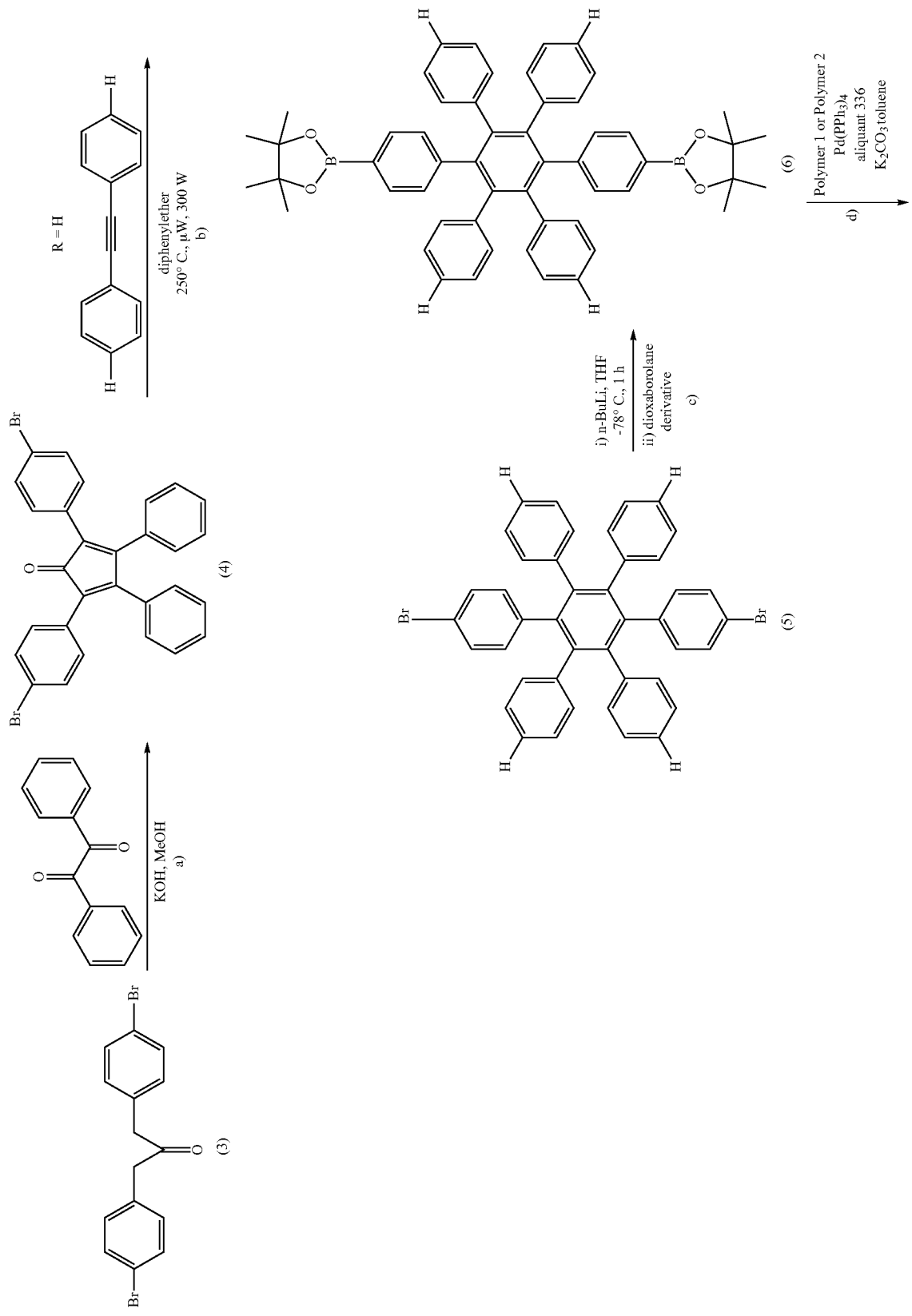

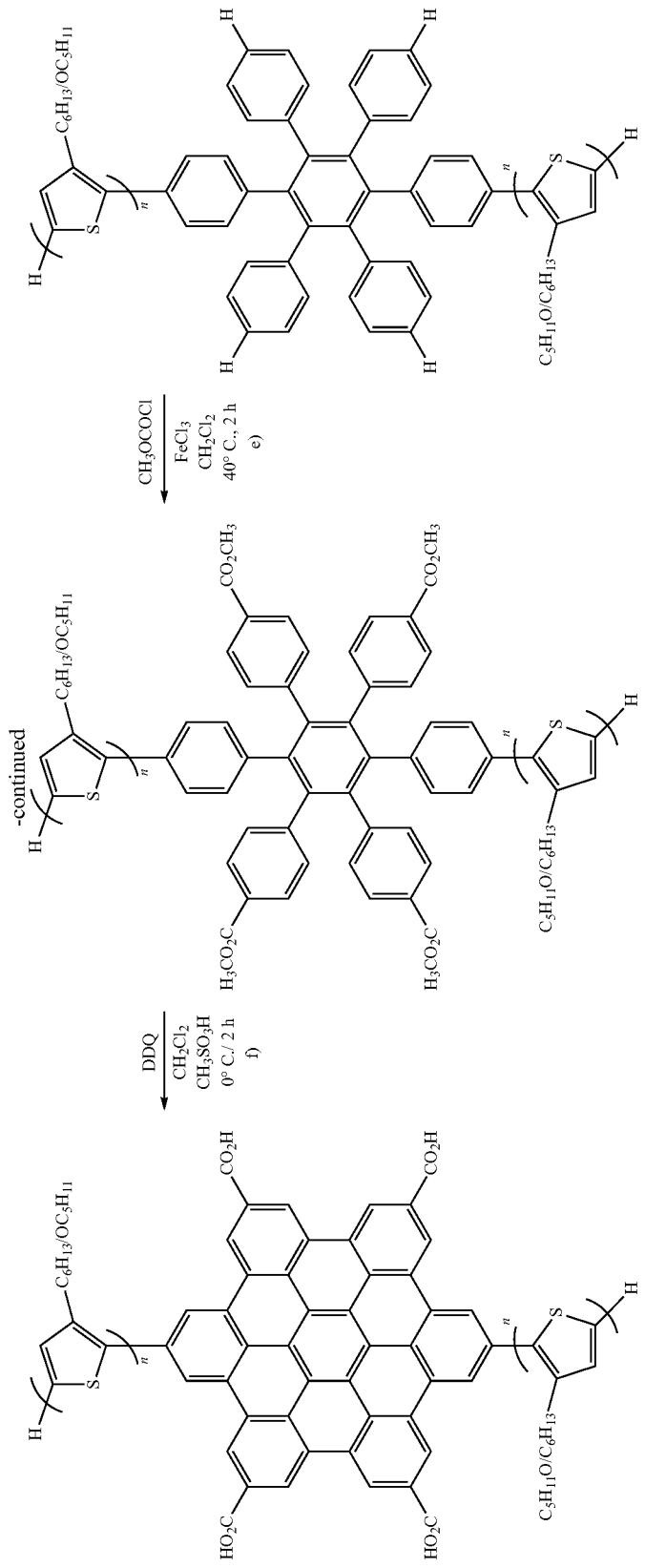

This first method of synthesis according to the invention comprises the following steps:

a) reaction of a compound of following formula (3):

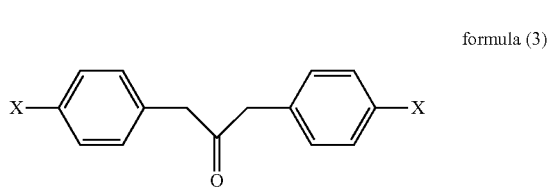

formula (3)

wherein X is a halogen chosen among Br and I, preferably X is Br, with an equimolar amount of 1,2 phenylethane-1,2 dione (benzil), thereby obtaining a compound of following formula (4):

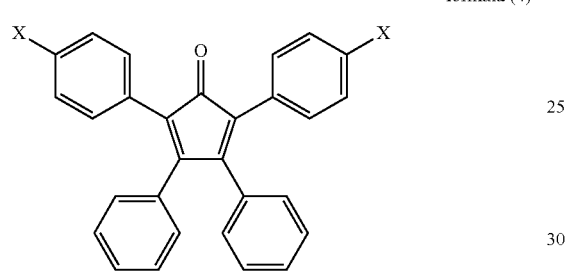

formula (4)

wherein X is as defined above, b) Diels-Alder reaction of the compound of formula (4) obtained in step a) with 1,2-bisphenylacetylene of following formula (4b):

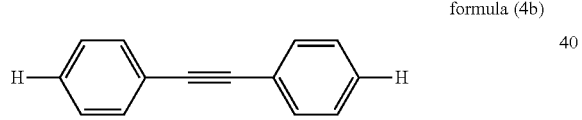

formula (4b)

thereby obtaining a compound of following formula (5):

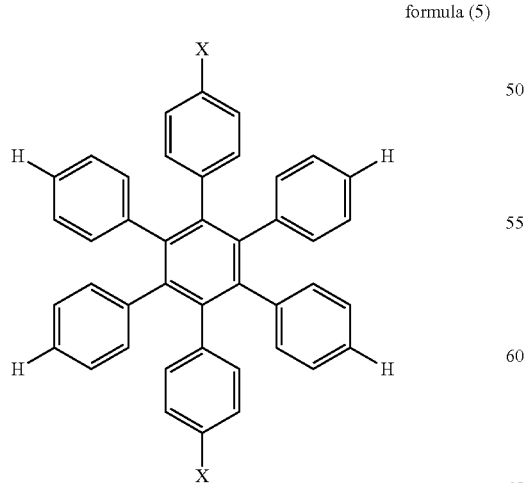

formula (5)

wherein X is as defined above, c) reaction of the compound of formula (5) obtained in step b) with a dioxaborolane derivative, thereby obtaining a compound of following formula (6):

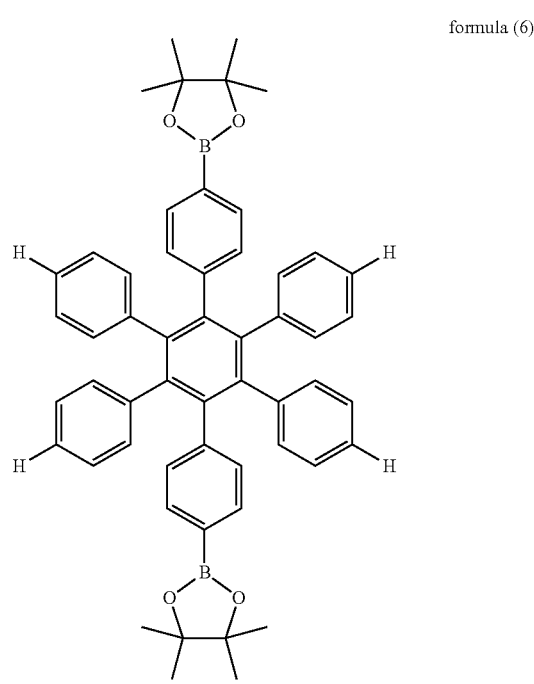 [SMILES: CC1(C)OB(c2ccc(-c3c(-c4ccccc4)c(-c4ccccc4)c(-c4ccc(B5OC(C)(C)C(C)(C)O5)cc4)c(-c4ccccc4)c3-c3ccccc3)cc2)OC1(C)C]

formula (6)

d) Suzuki-Miyaura coupling of the compound of formula (6) obtained in step c) with a polymer of following formula (1) or a polymer of following formula (2):

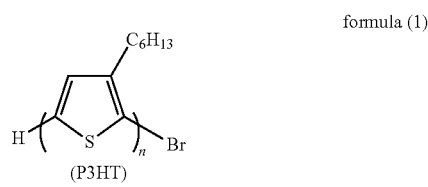

formula (1)

wherein n is comprised between 4 and 80 inclusive, preferably between 6 and 40 inclusive, and more preferably between 6 and 25 inclusive.

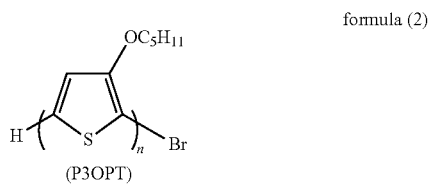

formula (2)

wherein n=is between 4 and 80 inclusive, and preferably between 6 and 40 inclusive, more preferably between 6 and 25 inclusive, thereby obtaining a compound of following formula (7) when the polymer has the above formula (1):

formula (7)

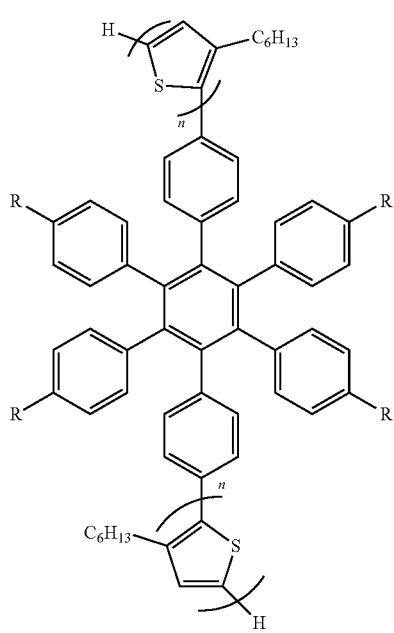

formula (9)

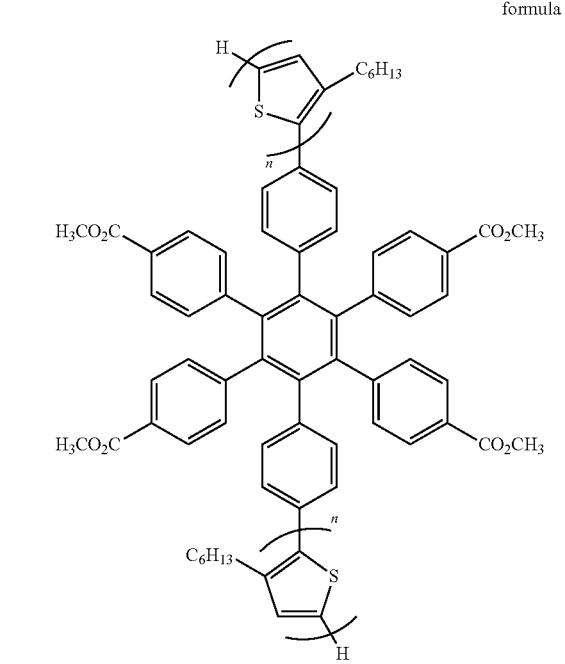

wherein n is comprised between 4 and 80 inclusive, preferably between 6 and 40 inclusive, and more preferably between 6 and 25 inclusive or a compound of following formula (8) when the polymer has the above formula (2):

formula (8)

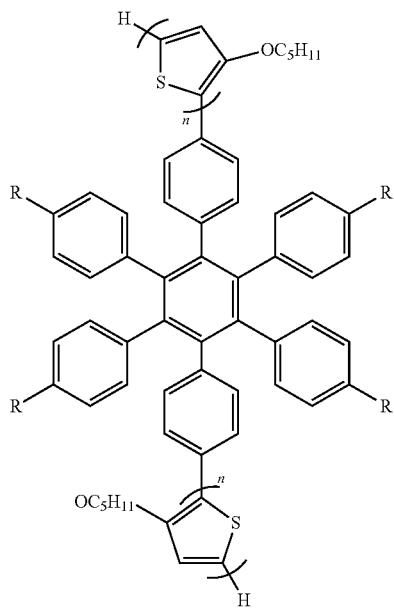

formula (10)

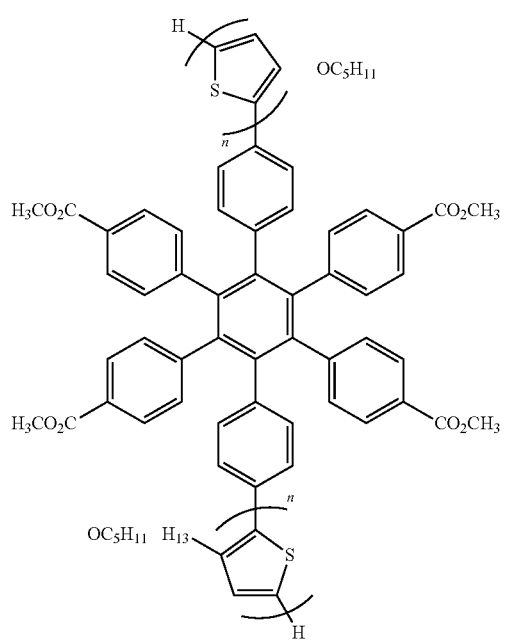

wherein n is comprised between 4 and 80 inclusive, preferably between 6 and 40 inclusive, and more preferably between 6 and 25 inclusive f) cyclodehydrogenation reaction of the compound of formula (9) or of the compound of formula (10) thereby obtaining the compound of formula I-1.

In this first method according to the invention, step e1) of introducing the carboxylic groups on the intermediate is carried out after the coupling of the polymer of formula (1) (P3HT) or of the polymer of formula (2) (P3OPT). And this grafting of the carboxylic groups is carried, in step e), by Friedel-Crafts acylation between an acid chloride and the compounds (7) or (8).

This Friedel-Crafts acylation could provoke attacks on the polymer chains grafted in step d), giving a lower yield.

wherein n is comprised between 4 and 80 inclusive, preferably between 6 and 40 inclusive, and more preferably between 6 and 25 inclusive e) Friedel-Crafts acylation between an acid chloride, preferably methyl carbonochloridate (methyl chloroformate), and the compound of formula (7) or the compound of formula (8) thereby obtaining the hexabenzocoronene-based compound of following formula (9) or (10):

In order to avoid such attacks on the polymer chain, a second process of the invention is a process wherein the introduction of the carboxylic groups is carried out before step e) of introduction of the polymer in the compound.

Thus, the invention proposes a second method of synthesis of the compound of formula I-1 comprising the following steps:

a) reaction of a compound of following formula (3):

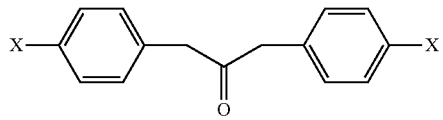

formula (3)

wherein X is a halogen chosen among Br and 1, preferably X is Br, with an equimolar amount of 1,2 phenylethan-1,2 dione (benzyl), thereby obtaining a compound of following formula (4):

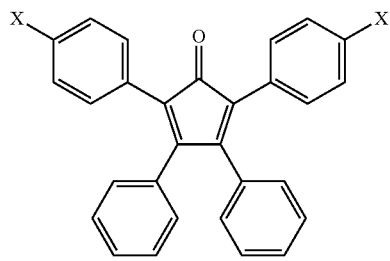

formula (4)

wherein X is as defined above, b) Diels-Alder reaction of the compound of formula (4) obtained in step a) with 1,2-bisphenylacetylene of following formula (4b):

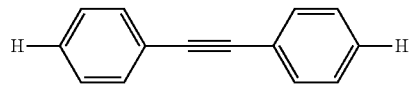

formula (4b)

thereby obtaining a compound of following formula (5):

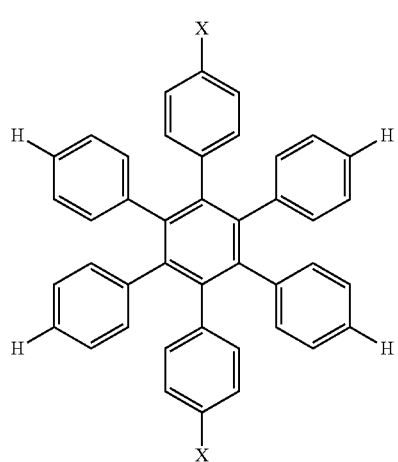

formula (5)

wherein X is as defined above, c) reaction of the compound of formula (5) obtained in step b) with a dioxaborolane derivative, thereby obtaining a compound of following formula (6):

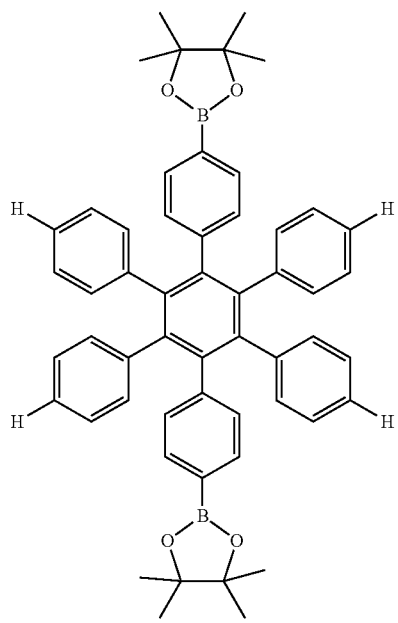

formula (6)

d1) Friedel-Crafts acylation between an acid chloride, preferably methyl carbonochloridate, and the compound of formula (6) obtained in step c) and tert-butyl chloride using as catalyst $FeCl_3$, thereby obtaining a compound of following formula (6'):

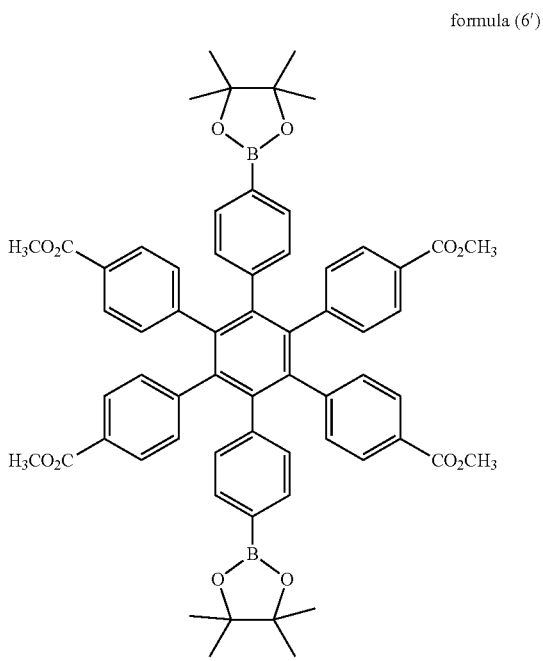 [SMILES: COC(=O)c1ccc(-c2c(-c3ccc(B4OC(C)(C)C(C)(C)O4)cc3)c(-c3ccc(C(=O)OC)cc3)c(-c3ccc(C(=O)OC)cc3)c(-c3ccc(B4OC(C)(C)C(C)(C)O4)cc3)c2-c2ccc(C(=O)OC)cc2)cc1]

formula (6')

e1) Suzuki-Miyaura coupling of the compound of formula (6') obtained in step d1) with a polymer of following formula (1) or of a polymer of following formula (2):

formula (1)

[Structure of P3HT: thiophene with C6H13 substituent, H and Br end groups, n repeating units]

(P3HT)

wherein n is comprised between 4 and 80 inclusive, preferably between 6 and 40 inclusive, and more preferably between 6 and 25 inclusive formula (2)

[Structure of P3OPT: thiophene with OC5H11 substituent, H and Br end groups, n repeating units]

(P3OPT)

wherein n is comprised between 4 and 80 inclusive, preferably between 6 and 40 inclusive, and more preferably between 6 and 25 inclusive thereby obtaining a compound of following formula (7') when the polymer has the above formula (1):

formula (7')

[Structure showing central benzene ring with six phenyl substituents bearing CO2CH3 groups (four) and thiophene-C6H13 groups (two) with n repeating units]

wherein n is comprised between 4 and 80 inclusive, preferably between 6 and 40 inclusive, and more preferably between 6 and 25 inclusive or a compound of following formula (8') when the polymer has the above formula (2)

formula (8')

[Structure showing central benzene ring with six phenyl substituents bearing CO2CH3 groups (four) and thiophene-OC5H11 groups (two) with n repeating units]

wherein n is comprised between 4 and 80 inclusive, preferably between 6 and 40 inclusive, and more preferably between 6 and 25 inclusive.

f) cyclodehydrogenation reaction of the compound of formula (7') or of the compound of formula (8'), thereby obtaining the compound of formula I-1.

Preferably, in the first and second methods of the invention, step f) of cyclodehydrogenation of the compound of formula (7') or of the compound of formula (8') or of the compound of formula (9) of the compound of formula (10), is carried out by reacting these compounds with 2,3-dichloro-5,6-dicyano-1,4-benzoquinone (DDQ).

But step f) may also be a step of reaction of the compound of formula (7') or the compound of formula (8') or of the compound of formula (9) or of the compound of formula (10) with $FeCl_3$, dissolved in $CH_3NO_2$.

In the first and second methods of synthesis of the invention, step f) of cyclodehydrogenation is carried out on the intermediate in which all the substituents $R^1$, $R^3$, $R^4$ and $R^5$ are already grafted.

The presence of these substituents may render the final cyclodehydrogenation less effective, so that a lower yield is obtained.

It is why the invention also proposes a third method of synthesis of the compound of formula I-1.

In this third method, the step of cyclodehydrogenation is carried out before introduction of the carboxylic groups and of polymers (1) or (2), i.e. after step c) of formation of the bis-boronic ester intermediate.

Accordingly, the third method of synthesis of the compound of formula I-1, according to the invention, comprises the following steps:

a) reaction of a compound of following formula (3):

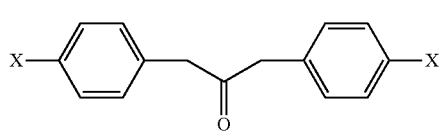

formula (3)

wherein X is a halogen chosen among Br and I, preferably X is Br, with an equimolar amount of 1,2 phenylethane-1,2 dione (benzyl), thereby obtaining a compound of following formula (4):

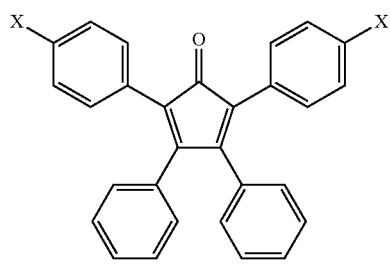

formula (4)

wherein X is as defined above, b) Diels-Alder reaction of the compound of formula (4) obtained in step a) with 1,2-bisphenylacetylene of following formula (4b):

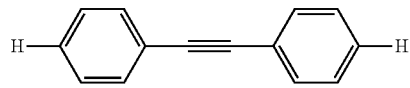

formula (4b)

thereby obtaining a compound of following formula (5):

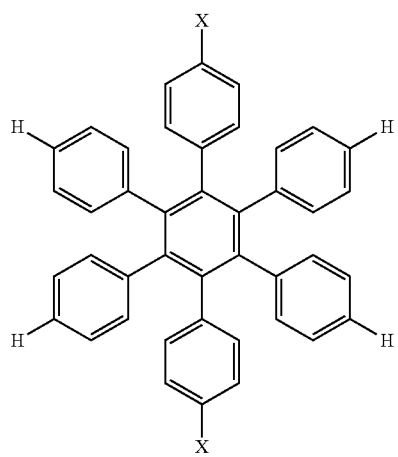

formula (5)

wherein X is as defined above, c) reaction of the compound of formula (5) obtained in step b) with a dioxaborolane derivative, thereby obtaining a compound of following formula (6):

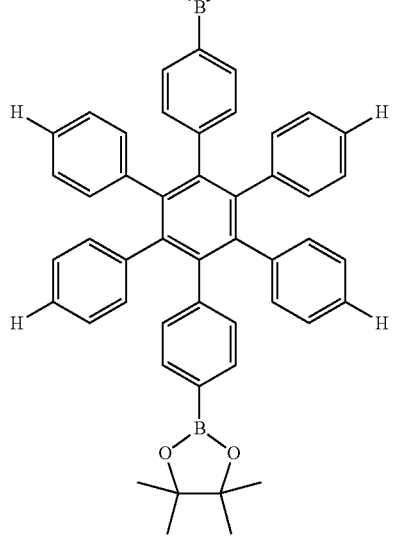

formula (6)

d) Suzuki-Miyaura coupling of the compound of formula (6) obtained in step c) with a polymer of following formula (1) or a polymer of following formula (2):

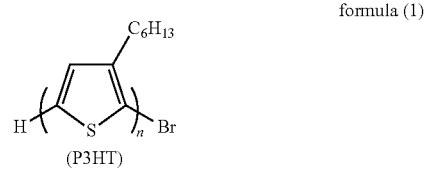

formula (1) (P3HT)

wherein n is comprised between 4 and 80 inclusive, preferably between 6 and 40 inclusive, and more preferably between 6 and 15 inclusive

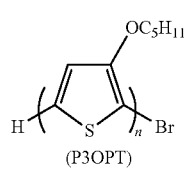

formula (2) (P3OPT)

wherein n is comprised between 4 and 80 inclusive, preferably between 6 and 40 inclusive, and more preferably between 6 and 25 inclusive, thereby obtaining a compound of following formula (7) when the polymer has the above formula (1)

formula (7)

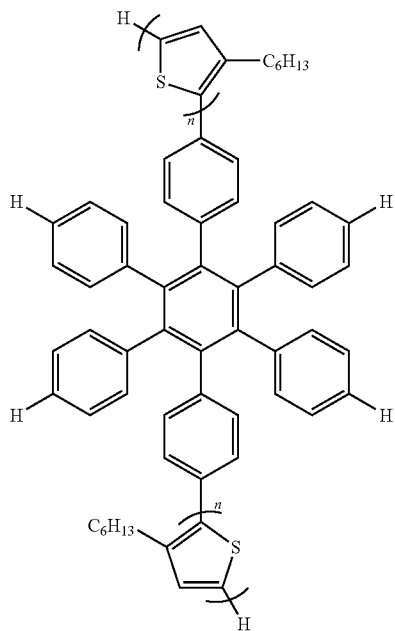

wherein n is comprised between 4 and 80 inclusive, preferably between 6 and 40 inclusive, and more preferably between 6 and 25 inclusive, or a compound of following formula (8) when the polymer has the above formula (2):

formula (8)

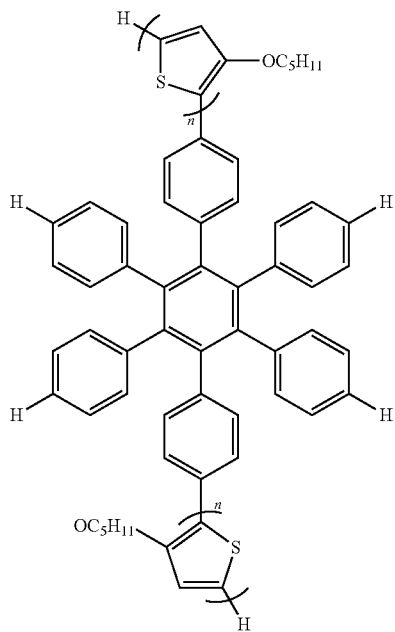

wherein n is comprised between 4 and 80 inclusive, preferably between 6 and 40 inclusive, and more preferably between 6 and 25 inclusive e2) cyclodehydrogenation of the compound of formula (7) or of the compound of formula (8) by reacting this compound with 2,3-dichloro-5,6-dicyano-1,4-benzoquinone (DDQ) or with $FeCl_3$ in $CH_3NO_2$, thereby obtaining the compound of following formula (13) when the polymer has the above formula (1):

formula (13)

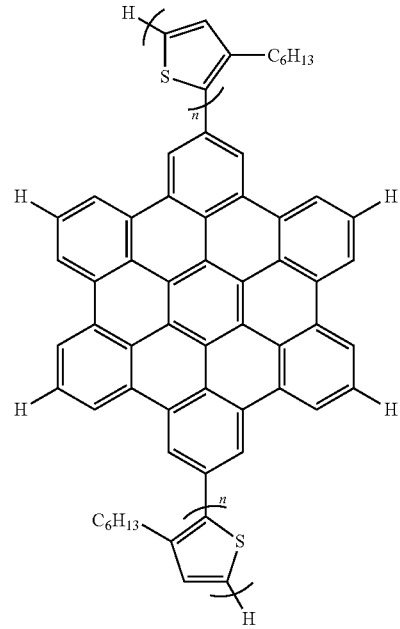

wherein n is comprised between 4 and 80 inclusive, preferably between 6 and 40 inclusive, and more preferably between 6 and 25 inclusive or a compound of following formula (14) when the polymer has the above formula (2):

formula (14)

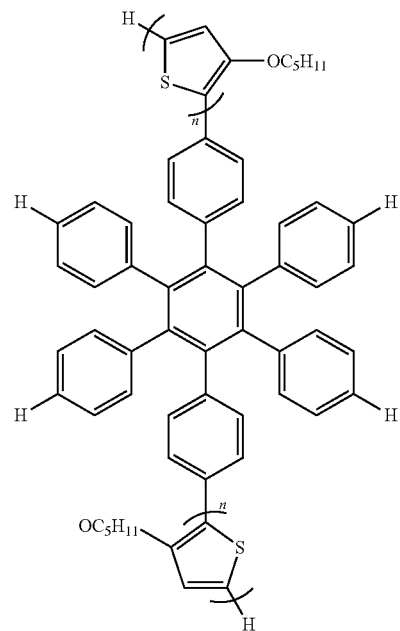

wherein n is comprised between 4 and 80 inclusive, preferably between 6 and 40 inclusive, and more preferably between 6 and 25 inclusive f1) Friedel-Crafts acylation between an acid chloride, preferably methyl carbonochloridate, or tert-butyl chloride, and the compound of formula (13) or the compound of formula (14), thereby obtaining the compound of formula I-1.

In all the methods of synthesis of the compound of formula I-1, according to the invention, preferably, in step c), the dioxaborolane derivative is 2-isopropoxy-4,4,5,5-tetramethyl-[1,3,2]dioxaborolane.

Also preferably, in all the method of synthesis of the compound of formula I-1, according to the invention, step b) is carried out in a microwave-heated apparatus at a temperature comprised between 200 and 256° C., preferably at 250° C. and a power of between 250 and 350 W, preferably at 300 W during between 60 and 300 minutes and preferably during 150 minutes.

All the methods of synthesis of the compound of formula I-1, according to the invention, may furthermore comprise a step g) of synthesis of the polymer of formula (1) (P3HT) or of the polymer of formula (2) (P3OPT).

Otherwise stated, step g) may be a step of synthesis of the polymer of formula (1) (P3HT) which is carried out by Grignard Metathesis (GRIM) polymerization of 2,5-dibromo-3-hexylthiophene or 2,5-diiodo-3-hexylthiophene or 2-bromo-5-iodo-3-hexylthiophene or 2-iodo-5-bromo-3-hexylthiophene but most preferably 2,5-dibromo-3-hexylthiophee But, step g) may also be a step of synthesis of polymer (2) (P3OPT) by the Grignard Metathesis (GRIM) polymerization of 2,5-dibromo(3-oxypentylthiophene) or 2,5-diiodo-(3-oxypentylthiophene) or 2-bromo-5-iodo-(3-oxypentylthiophene) or 2-iodo-5-bromo-(3-oxypentylthiophene) but most preferably 2,5-dibromo-(3-oxypentylthiophene).

In order to give a better understanding of the method of the invention, examples of synthesis of the compound of formula I-1 are given below.

Example 1: Step g) Synthesis of Polymer (1) which is poly(3-hexylthiophene) (P3HT)

This reaction is carried out according to the following reaction schema:

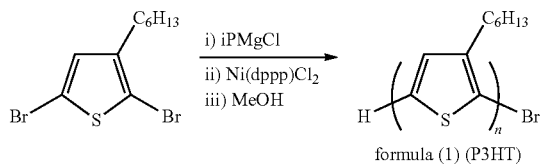

formula (1) (P3HT)

The synthesis of polymer 1 is carried out by a Grignard Metathesis (GRIM) polymerization of 2,5-dibromo(3-hexylthiophene) yielding to alpha-bromo-poly(3-hexylthiophene (P3HT) in which n may vary from is between 4 and 80 and preferably between 15 and 40 and ideally between 20 and 30. This GRIM polymerization is carried out according to the method described by J. Liu, R. S. Loewe, R. D. McCullough, *Macromolecules* 1999, 32, 5777.

Into a 100 mL flask equipped with a stirring bar is stirred for 2 h at 25° C. a mixture of 2,5-dibromo-3-hexylthiophene (0.6 mL, 0.40 g, 1.2×10⁻³ mol), freshly distilled THF (2.4 mL) and isopropyl magnesium chloride (2 Min THF, 0.6 mL, 1.2×10⁻³ mol). The solution is diluted with THP (8 mL) prior to the one-shot addition of 1,3-bis(diphenylphosphino)propane nickel(II) chloride [Ni(dppp)Cl$_2$] (6×10⁻⁵ mol). The polymerisation is stirred for 60 min, and terminated by the addition of 2 mL of HCl (5 M). The solution is dropped into methanol (100 mL) and filtered into a Soxhlet thimble. The purple polymer is Soxhlet washed with methanol, then hexane, and Soxhlet recovered with THF. The polymer is then precipitated three times from THF in methanol and recovered over a glass frit.

Example 2: Synthesis of Polymer of Formula (2) which is alpha-bromo-poly(3-oxypentylthiophene (P3OPT)

This synthesis is carried out according to the following reaction schema:

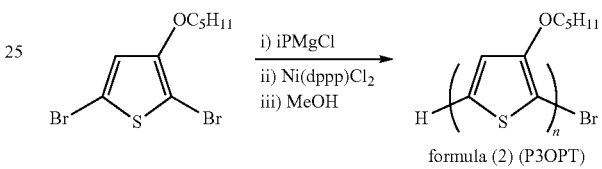

formula (2) (P3OPT)

The synthesis of polymer (2) is a Grignard Metathesis (GRIM) polymerization of 2.5-dibromo(3-oxypentylthiophene) yielding polymer 2 wherein n is comprised between 4 and 80, inclusive, preferably between 6 and 40, inclusive, and more preferably between 6 and 25, inclusive.

This GRIM polymerization is carried out as disclosed in J. Liu, R. S. Loewe, R. D. McCullough, *Macromolecules* 1999, 32, 5777.

Into a 100 mL flask equipped with a stirring bar is stirred for 2 h at 25° C. a mixture of 2,5-dibromo-3-oxypentylthiophene (1.2×10⁻³ mol), freshly distilled THF (2.4 mL) and isopropyl magnesium chloride (2 M in THF, 0.6 mL, 1.2×10⁻³ mol). The solution is diluted with THF (8 mL) prior to the one-shot addition of 1,3-bis(diphenylphosphino)propane nickel(II) chloride [Ni(dppp)Cl$_2$] (6×10⁻⁵ mol). The polymerisation is stirred for 60 min, and terminated by the addition of 2 mL of HCl (5 M). The solution is dropped into methanol (100 mL) and filtered into a Soxhlet thimble. The purple polymer is Soxhlet washed with methanol, then hexane, and Soxhlet recovered with THF. The polymer is then precipitated three times from THF in methanol and recovered over a glass frit.

Example 3: Synthesis of the Hexabenzocoronene-Based Compound of Formula I-1 Using the First Method of the Invention The reaction schema used in this example is the following:

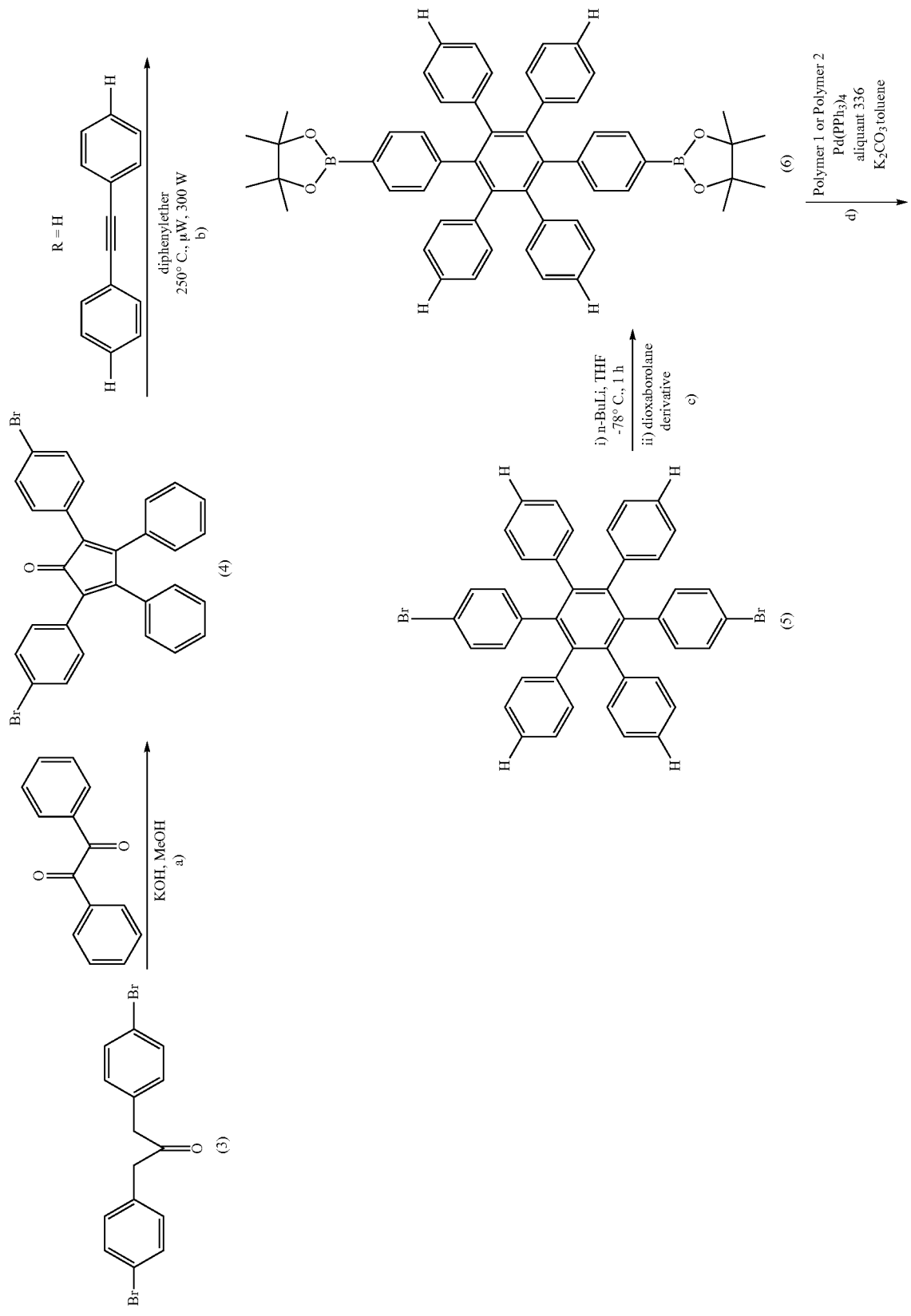

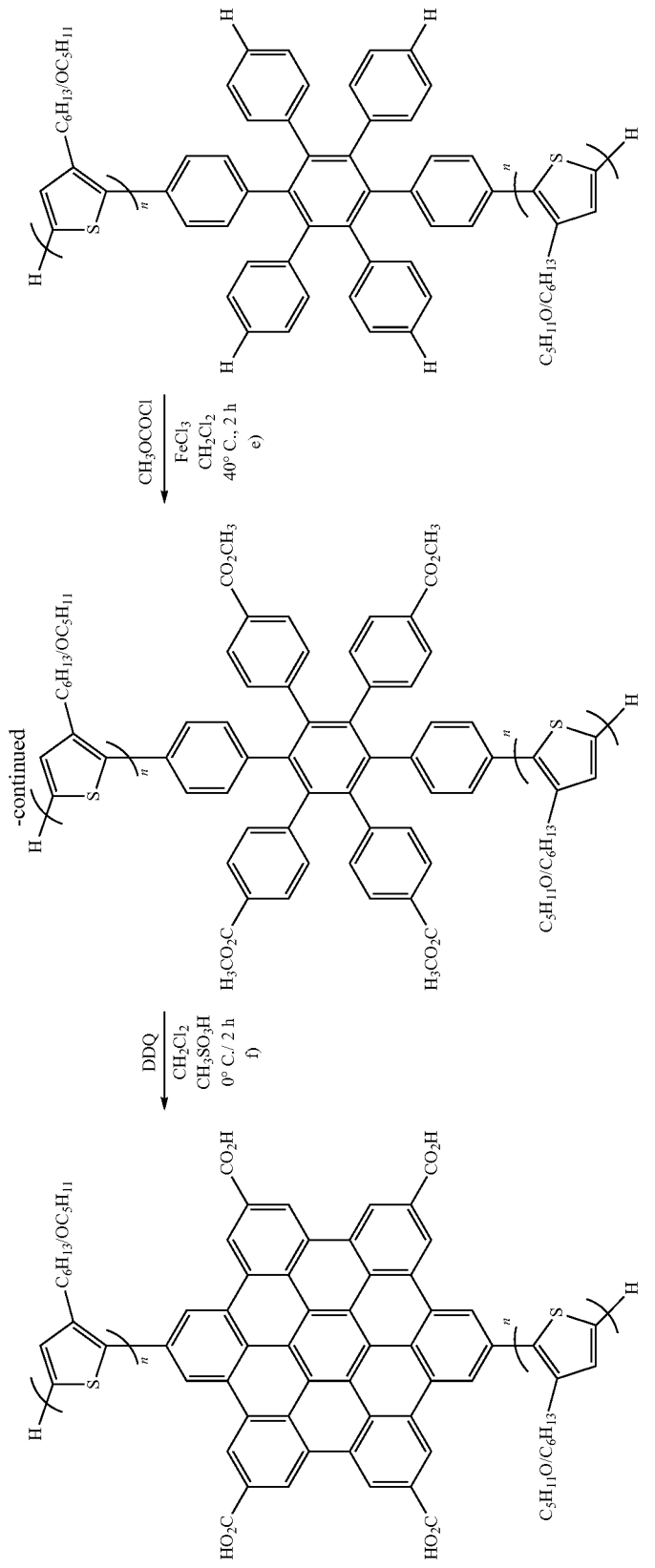

Step a): Reaction of 1,3-bis(4-bromophenyl)-2-propanone (3) and benzyl leading to 2,5-bis(4-bromophenyl)-3,4-diphenylcyclopenta-2,4-dienone (4)

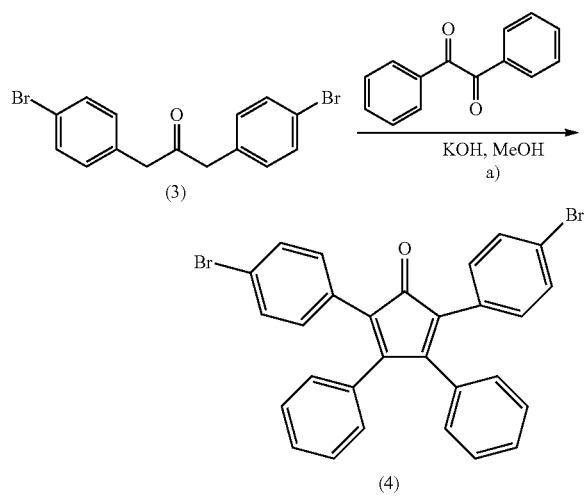

This reaction is carried out according to the method disclosed in C. M. Thompson, G. T. McCandless, S. N. Wijenayake, O. Alfarawati, M. Jahangiri, A. Kokash, Z. Tran, R. A. Smaldone, *Macromolecules* 2014, 47, 8645-8652.

To a 50 cm³ round-bottom flask containing 1,3-bis(4-bromophenyl)-2-propanone (3, 300 mg, 0.815 mmol) and benzyl (0.815 mmol) in dichloromethane (1.5 mL) is added potassium hydroxide (22.8 mg, 0.407 mmol) as a solution in methanol (3 mL). The reaction is heated to reflux under nitrogen for 90 min before being cooled in an ice bath. The mixture is introduced into 50 mL of ice cold methanol and the resulting solid 2,5-bis(4-bromophenyl)-3,4-diphenylcyclopenta-2,4-dienone (4) is filtered to provide a dark purple solid (404 mg, 91% yield). ¹H NMR (400.6 MHz, CDCl₃, ppm): δ 6.93 (d, 4H, J=7.6 Hz), 7.13 (d, 4H, J=8.8 Hz), 7.22 (t, 4H, J=7.2 Hz), 7.30 (t, 2H, J=7.6 Hz), 7.39 (d, 4H, J=8.8 Hz). ¹³C NMR (100.16 MHz, CDCl₃, ppm): δ 122.00 (s, aromatic), 124.38 (s, aromatic), 128.23 (s, aromatic), 128.89 (s, aromatic), 129.16 (s, aromatic), 129.51 (s, aromatic), 131.34 (s, aromatic), 131.64 (s, aromatic), 132.59 (s, aromatic), 155.02 (s, aromatic-Br), 199.52 (s, aromatic=O).

In this step a), 1,3-bis(4-chlorophenyl)-2-propane or 1,3-bis(4-iodophenyl)-2-propane may also be used as starting compound (3) leading to the corresponding chlorinated or iodinated compound (4).

Step b): Diels-Alder Reaction of 2,5-bis(4-bromophenyl)-3,4-dipbenylcyclopenta-2,4-dienone (4) with 1,2-bisphenylacetylene to yield 1,4-di(4-bromophenyl)-2,3,5,6-phenylbenzene (5)

The reaction schema of this step is the following:

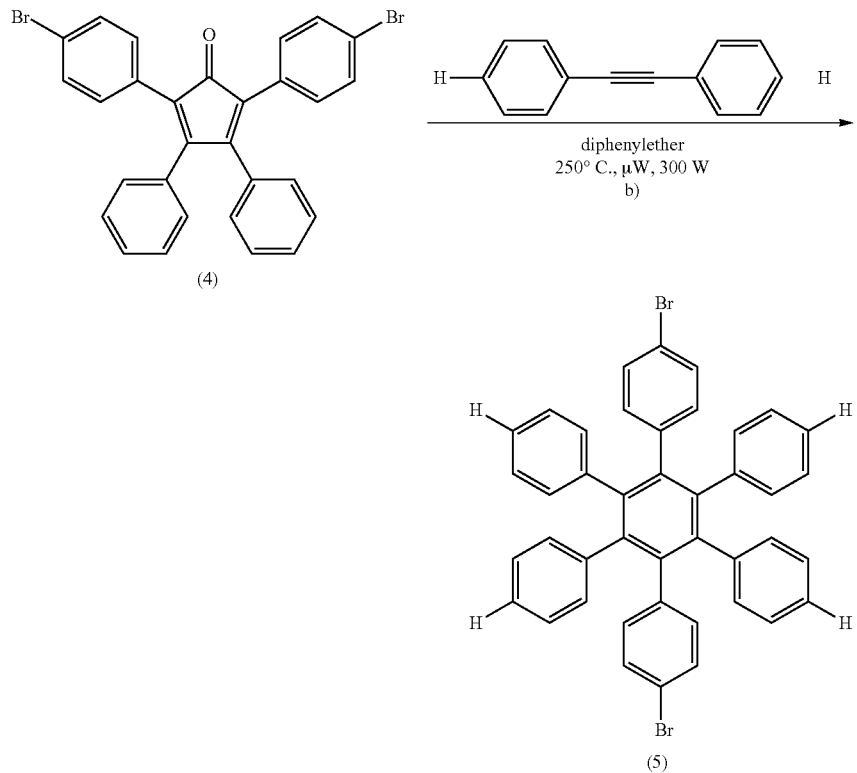

This reaction is carried out according to the method disclosed in A. Fechtenkotter, N. Tehebotareva, M. Watson, K. Müllen *Tetrahedron*, 2001, 57(17), 3769-3783.

To a microwave vial containing 4 (372 mg, 0.686 mmol) in diphenyl ether (2 mL) is added 1,2-bisphenylacetylene (122 mg, 0.686 mmol). This is microwave-heated (250° C.

and 300 W) for 150 min. The vial is cooled with a positive pressure of air, and the resulting purple slurry is filtered and washed with 10 mL of diphenyl ether. Dichloromethane is used to dissolve and recover all the products present on the paper filter and the solvent is evaporated. Methanol is added to remove diphenyl ether and the solution is filtered to yield 1,4-di(4-bromophenyl)-2,3,5,6-phenylbenzene (5) as white crystals (327 mg, 69% yield). $^1$H NMR (400.6 MHz, CDCl$_3$, ppm): δ 6.70 (d, 4H, J=8.4 Hz), 6.81 (d, 8H, J=7.2 Hz), 6.90 (t, 8H, J=2.4 Hz), 6.91 (t, 4H, J=4 Hz), 7.00 (d, 4H, J=8.4 Hz). $^{13}$C NMR (100.16 MHz, CDCl$_3$, ppm): δ 119.53 (s, aromatic-Br), 125.54 (s, aromatic), 126.86 (s, aromatic), 129.82 (s, aromatic), 131.25 (s, aromatic), 132.93 (s, aromatic), 139.34 (s, aromatic), 139.53 (s, aromatic), 140.07 (s, aromatic), 140.40 (s, aromatic). Compound (5) is also known as 4-bromo-4'-(4-bromophenyl)-3',5',6'-triphenyl-1,1';2',1''-terphenyl.

Step c): Formation of the bis-boronic ester Compound (6) called 2,2'-(2',3',5',6'-tetraphenyl-[1,1':4',1''-terphenyl]-4,4''-diyl)bis(4,4,5,5-tetramethyl-1,3,2-dioxaborolante)

The reaction schema of this step is the following:

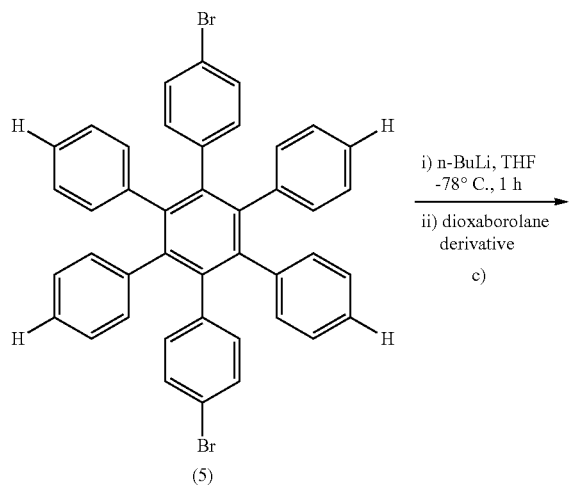

This reaction is carried out according to the method disclosed in X. Yang, X. Dou, A. Rouhanipour, L. Zhi, H. J. Räder, K. Müllen, *J. Am. Chem. Soc.,* 2008, 130, 4216-4217.

To a solution of compound 5 (0.14 mmol) in dry THF (2.4 mL) under nitrogen at −78° C., n-BuLi (2.5 M/n-hexane, 0.36 mmol) is added and the resulting solution is stirred at −78° C. for 30 minutes and then left to warm to 0° C. and held there for 15 minutes. Then the solution is cooled to −78° C. and 2-isopropoxy-4,4,5,5-tetramethyl-[1,3,2]dioxaborolane (0.42 mmol) is added and the reaction is stirred at −78° C. for 15 minutes and then the cooling bath is removed so that the solution warms to room temperature while stirring for 90 minutes. The reaction is quenched with water (5 mL) and the resulting mixture is extracted with dichloromethane. The combined organic layers are washed with brine, dried with MgSO$_4$ and concentrated under reduced pressure. The residue is purified by passing through a column (silica gel, aluminium oxide, dichloromethane) to give compound 6 as a white solid, yield 5%).

Step d): Suzuki-Miyaura Coupling of Compound (6) and Polymer 1 or Polymer 2 Leading to Copolymers poly(3-hexylthiophene)-block-hexaphenyl-benzene-block-poly(3-hexylthiophene) (7) or poly(3-oxypentylthiophene)-block-hexaphenylbenzene-block-poly(3-oxypentylthiophene) (8)

The reaction schema of this Suzuki-Miyaura coupling is the following:

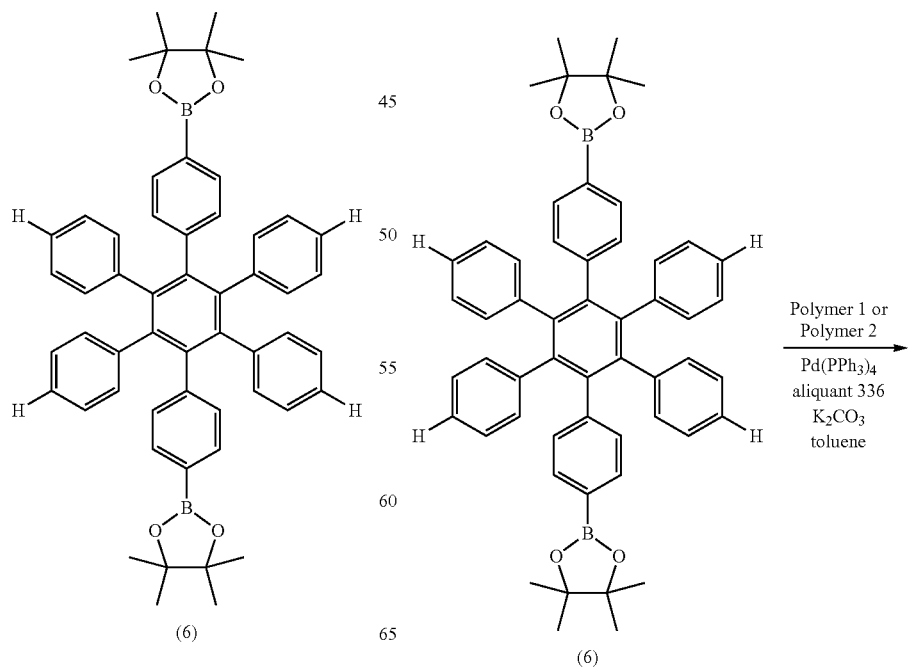

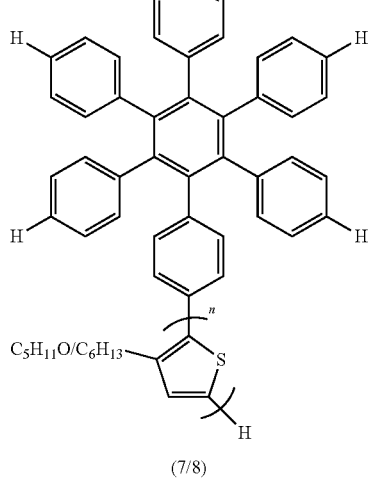

(7/8)

This reaction is carried out according to the method disclosed in X. Yang, X. Dou, A. Rouhanipour, L. Zhi, H. J. Räder, K. Müllen, J. Am. Chem. Soc., 2008, 130, 4216-4217.

The method disclosed in this document has been changed by way of adding a polymer in place of small molecules.

A mixture of compound 1 or 2 (0.074 mmol), compound 6 (0.074 mmol), $K_2CO_3$ (2 M/$H_2O$, 2 mL, 4 mmol) and Aliquat® 336 (0.6 mg, 0.0015 mmol) in toluene (5 mL) is degassed three times via 'freeze-pump-thaw' cycles. $Pd(PPh_3)_4$ (0.004 mmol) is added quickly and the reaction mixture degassed three times again via 'freeze-pump-thaw' cycles. The reaction is refluxed under argon for 3 days. Then, a degassed solution of 1 or 2 (0.074 mmol) in toluene (1 mL) is added into the reaction mixture via a syringe.

The reaction mixture is poured into a mixture of methanol (200 mL) and concentrated aqueous HCl solution (30 mL) and stirred overnight. The resulting black solid is filtered off and subjected to Soxhlet extraction for 2 days in acetone. The residue is redissolved in hot THF and precipitated again in methanol. The solid is filtered, washed with methanol and dried in vacuum to give polymers 7/8.

Step e): Friedel-Crafts Acylation Between an Acid Chloride and Compounds (7) or (8) Leading to the Synthesis of Compounds (9) or (10)

The reaction schema of this step is the following:

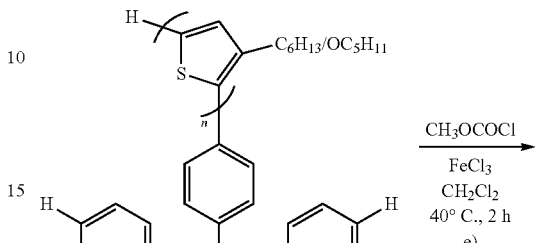

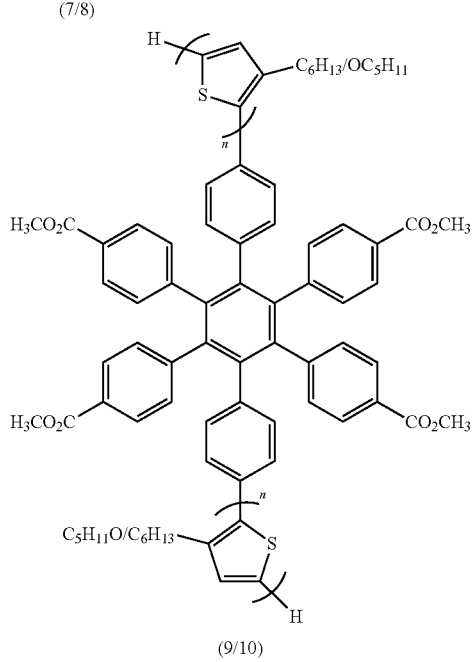

(9/10)

Into a nitrogen flushed vessel containing 7 or 8 (1.44 mmol) in dichloromethane (10 mL) is added $CH_3COCl$ (28.8 mmol) followed by a solution of $FeCl_3$ (1.6 mmol) in dichloromethane (10 mL). The solution is stirred under reflux for 2 h. After that time the reaction is filtered, and the resulting solid is dissolved in dichloromethane (30 mL) and precipitated in methanol (300 mL), and reprecipitated in the same manner, and dried under reduced pressure to the final product.

Step f): Cyclodehydrogenation Reaction of Compound (9) or (10) Leading to Compound (11) or (12)

The reaction schema of this step is the following:

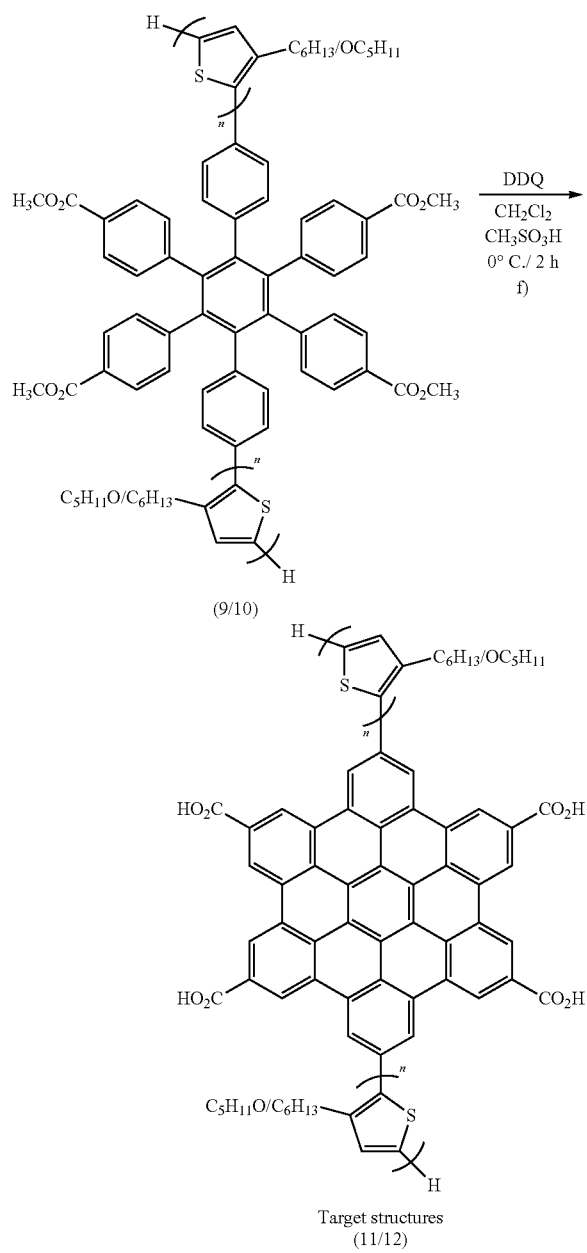

This reaction is based on the method disclosed in L. Zhai, R. Shukla, R. Rathore, *Org. Lett.* 2009, 11, 3474-3477.

A solution of 9 or 10 in dichloromethane (10 mL) containing protic acid (10% v/v) or Lewis acid (~10 equiv.) at ~0° C. is treated with DDQ (1 equivalent per C—C bond formation), and the solution immediately took on a dark-green coloration. The progress of the reaction is monitored by TLC and $^1$H NMR spectroscopy. After completion of the reaction, it was quenched with a saturated aqueous solution of NaHCO$_3$ (20 mL). The dichloromethane layer was separated and washed with water and brine solution and dried over anhydrous MgSO$_4$ and filtered. Removal of the solvent in vacuo afforded the crude product.

Example 4: Synthesis of the Target Compounds of Formula I-1 by the Second Method of Synthesis of the Invention This method is used in order to avoid attacks on the polymer chains present in compound (7) or (8) obtained in examples 3 and 4 during step e).

As already stated, in order to avoid such attacks, the introduction of the carboxylic groups (step e) of the first method of synthesis according to the invention) is carried out before step d) of the first method of synthesis of introduction of the polymers in the intermediate compound.

Into a nitrogen flushed vessel containing 6 (1.44 mmol) in dichloromethane (10 mL) is added CH$_3$COCl (28.8 mmol) followed by a solution of FeCl$_3$ (1.6 mmol) in dichloromethane (10 mL). The solution is stirred under reflux for 2 h. After that time the reaction is filtered, and the resulting solid is dissolved in dichloromethane (30 mL) and precipitated in methanol (300 mL), and reprecipitated in the same manner, and dried under reduced pressure to the final product.

Then, the step of introduction of the polymer in the intermediate compound thus obtained is carried out and the other steps are the same as in the first method of the invention.

Example 5

In this example, the final step of cyclodehydrogenation of the first and second methods of synthesis of the invention is carried out before the introduction of the carboxylic groups.

Thus, step noted f) in the first and second method of the invention is carried out, in the third method of the invention, after step d) of the first method of the invention or after d1) of the second method of the invention, and step e) of the first method of the invention and step e1) of the second method of the invention is the final step.

This step of cyclodehydrogenation is noted e2) in the third method of the invention. This step is followed by the step of introduction of the carboxylic groups by Friedel-Crafts acylation noted f1) in the third method of the invention.

In the third method of the invention, step e2) is carried out as follows,

A 250 mL two necked round bottom flask is charged with 0.36 mmol of 7 or 8 with 100 mL of CH$_2$Cl$_2$. The solution is flushed with argon. FeCl$_3$ (6.9 mmol) dissolved in CH$_3$NO$_2$ (13 mL) is added dropwise. After 30 min, the mixture is quenched with a large excess of methanol and the precipitate is filtered. The resulting yellow solid is redissolved in dichloromethane and filtered through a short pad of silica gel and dried under vacuum.

Step a) to d) are the same as in the first method of the invention.

Example 6

The Voc (Open circuit Voltage) and $\Delta E^{LUMO}$ of the compounds obtained in examples 3-6 have been determined.

These Voc and $\Delta E^{LUMO}$ values of compounds of examples 3-6 are reported in following table 2, together with the Voc and $\Delta E^{LUMO}$ of compounds 10b and 10c of Jones et al. and of a non substituted HBC.

TABLE 2

| Compound | $V_{oc}$ (eV) vs. donor | | $\Delta E^{LUMO}$ (eV) vs. donor | |
| --- | --- | --- | --- | --- |
| | P3HT | P3OPT | P3HT | P3OPT |
| Example 3 | 1.15 | 0.79 | 0.55 | 0.32 |
| Example 4 | 1.15 | 0.79 | 0.55 | 0.32 |
| Example 5 | 1.15 | 0.79 | 0.55 | 0.32 |
| Example 6 | 1.15 | 0.79 | 0.55 | 0.32 |
| Compound 10c of Jones et al | | | >1 | >1 |
| Compound 10b of Jones et al | | | >1 | >1 |
| HBC in which $R^1$, $R^2$, $R^3$, $R^4$, $R^5$ and $R^6$ are H | 2.35 | 1.99 | −0.35 | −0.58 |

As can be seen from table 2, the compounds 10c and 10b exhibit $\Delta E^{LUMO}$ which is superior to 1 eV, so that they are not candidates for OPV devices and the $\Delta E^{LUMO}$ of the HBC in which $R^1$, $R^2$, $R^3$, $R^4$, $R^5$ and $R^6$ is to low. In contrast, the $\Delta E^{LUMO}$ of the compounds of the invention are close to 0.3 eV.

These results clearly demonstrate that the compounds of the invention which have a columnar structure are the best adapted for obtaining an ideal Voc, due to the particular choice of the $R^1$, $R^3$, $R^4$ and $R^6$ substituents and that this particular choice associated with the particular choice of the $R^2$ and $R^5$ substituents permits an ideal and simultaneous transfer of charges between the donor and the acceptor in an OPV device.

The Voc (Open circuit Voltage) of the compounds obtained in examples 3-6 and of the compounds 10b and 10c of Jones et al. as well as of the HBC in which all the substituents are H, are determined using the method disclosed in the article of G. E. Morse, A. Tournebize, A. Rivaton, T. Chassé, C. Taviot-Guého, N. Blouin, O. R. Lozman, S. Tierney, *Phys. Chem. Chem. Phys.* 2015, 17, 11884.

The invention claimed is:

1. A Hexabenzocoronene-based compound of following formula I:

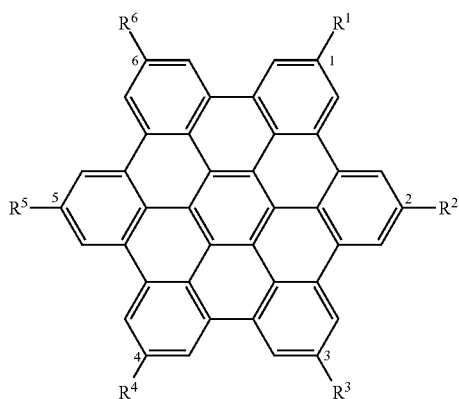

wherein $R^1$, $R^3$, $R^4$ and $R^6$ are independently from each other chosen among a carboxylic (—COOH) group, a cyano (—C≡N) group, an isocyano (—N$^+$≡C$^-$) group, a cyanate (—O—C≡N) group and a —F group, and $R^2$ and $R^5$ are, independently from each other, chosen among a poly(3-oxypentylthiophene) (P3OPT) substituent and a poly(3-hexylthiophene) (P3HT) substituent.

2. The hexabenzocoronene-based compound of claim 1, wherein $R^1$, $R^3$, $R^4$ and $R^6$ are identical.

3. The hexabenzocoronene-based compound of claim 1, wherein $R^2$ and $R^5$ are identical and are a poly(3-oxypentylthiophene) substituent.

4. The hexabenzocoronene-based compound of claim 1, wherein $R^2$ and $R^5$ are identical and are a poly(3-hexylthiophene) substituent.

5. The hexabenzocoronene-based compound according to claim 1, wherein $R^1$, $R^3$, $R^4$ and $R^6$ are identical and are carboxylic groups.

6. The hexabenzocoronene-based compound according to claim 1, having the following formula I-1:

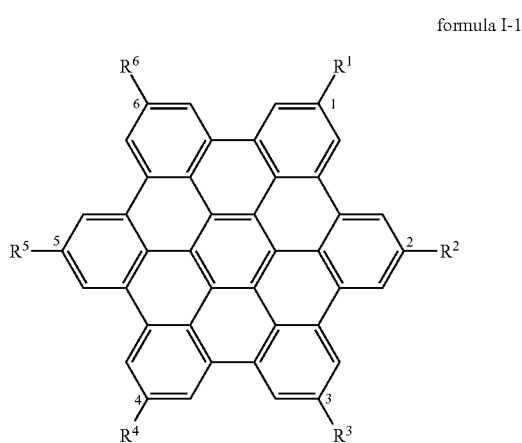

formula I-1 wherein $R^1$, $R^3$, $R^4$ and $R^6$ are identical and are a carboxylic group (—COOH), and $R^2$ and $R^5$ are identical and are chosen among a poly(3-oxypentylthiophene) (P3OPT) substituent and a poly(3-hexylthiophene) (P3HT) substituent.

7. A method of synthesis of a hexabenzocoronene-based compound according to claim 6 of following formula I-1:

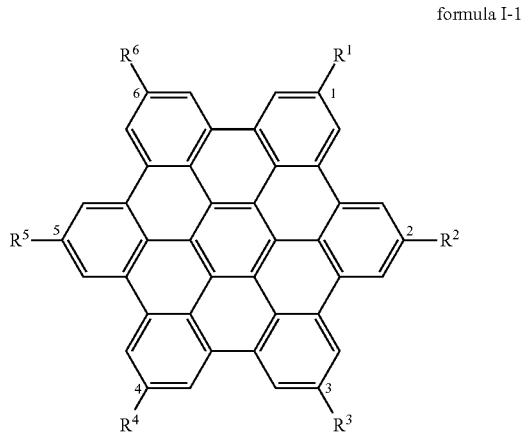

formula I-1 wherein $R^1$, $R^3$, $R^4$ and $R^6$ are identical and are a carboxylic group (—COOH), and $R^2$ and $R^5$ are identical and are chosen among a poly(3-oxypentylthiophene) (P3OPT) substituent and a poly(3-hexylthiophene) (P3HT), the method comprising the following steps:
a) reaction of a compound of following formula (3):

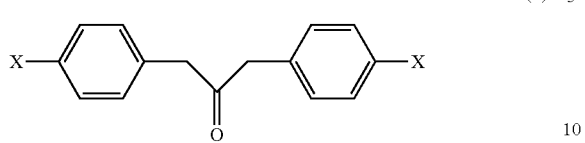

formula (3)

wherein X is a halogen chosen among Br, Cl and I with an equimolar amount of 1,2 phenylethan-1,2 dione (benzil),
thereby obtaining a compound of following formula (4):

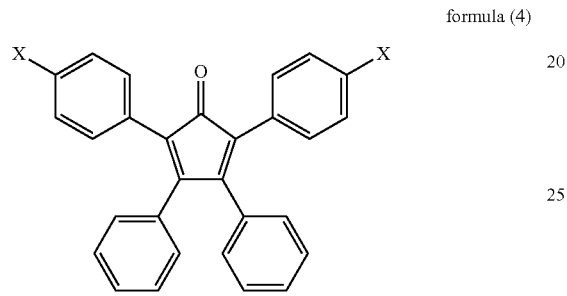

formula (4)

wherein X is as defined above,
b) Diels-Alder reaction of the compound of formula (4) obtained in step a) with 1,2-bisphenylacetylene of following formula (4b):

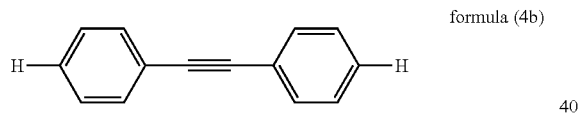

formula (4b)

thereby obtaining a compound of following formula (5):

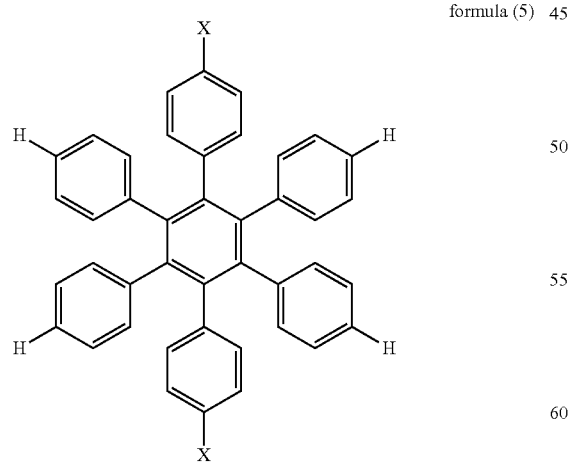

formula (5)

wherein X is as defined above,
c) reacting of compound of formula (5) obtained in step b) with a dioxaborolane derivative, thereby obtaining a compound of following formula (6):

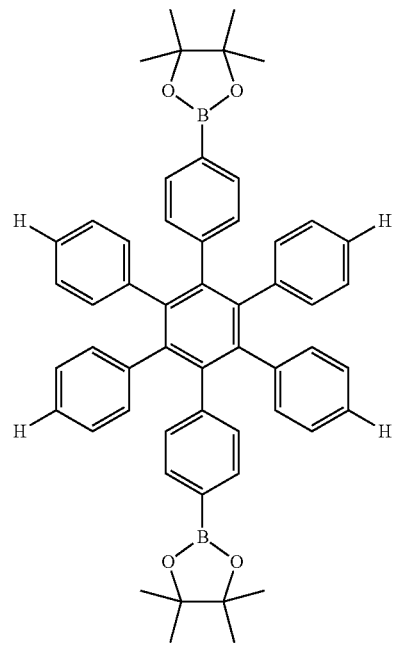

formula (6)

d) Suzuki-Miyaura coupling of the compound of formula (6) obtained in step c) with a polymer of following formula (1) or a polymer of following formula (2):

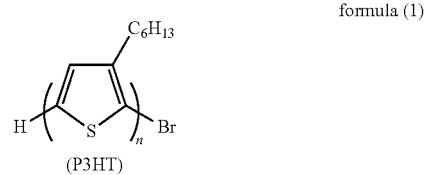

formula (1)

(P3HT)

wherein n is comprised between 4 and 80

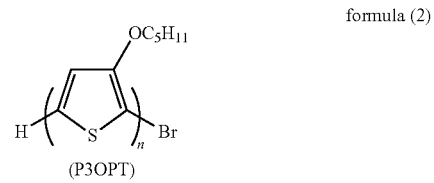

formula (2)

(P3OPT)

wherein n is comprised between 4 and 80
thereby obtaining a compound of following formula (7) when the polymer has the above formula (1):

formula (7)

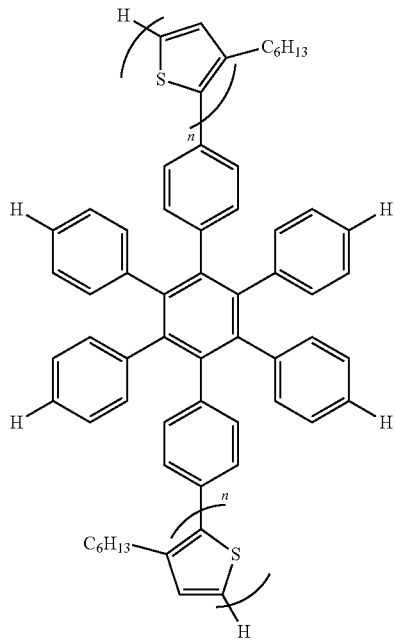

wherein n is comprised between 4 and 80 or a compound of following formula (8) when the polymer has the above formula (2):

formula (8)

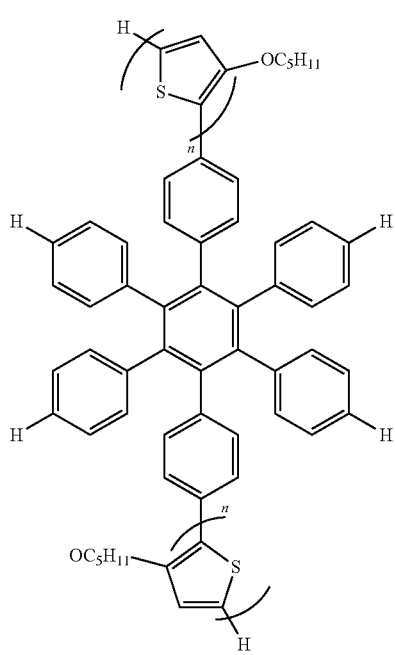

wherein n is comprised between 4 and 80 e) Friedel-Crafts acylation between an acid chloride and the compound of formula (7) or the compound of formula (8), thereby obtaining the hexabenzocoronene-based compound of following formula (9) or (10):

formula (9)

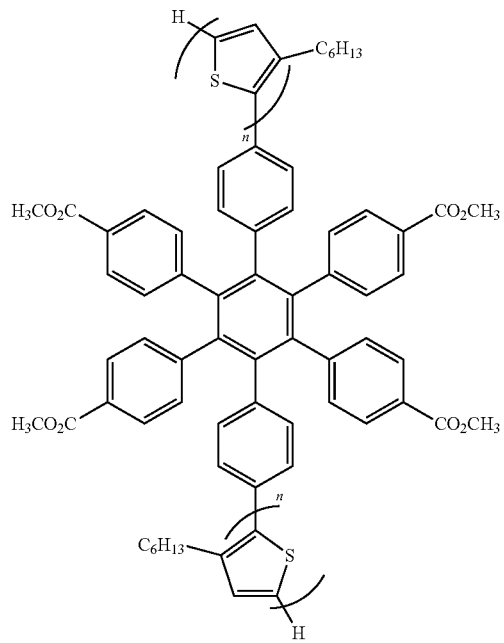

wherein n is comprised between 4 and 80 formula (10)

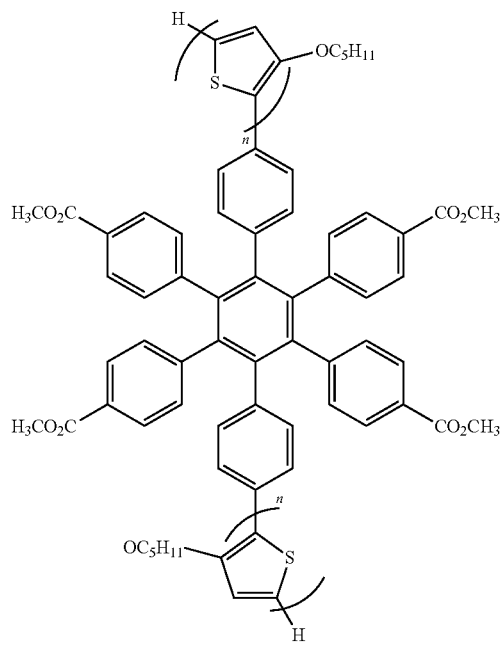

wherein n is comprised between 4 and 80 f) cyclodehydrogenation reaction of the compound of formula (9) or of the compound of formula (10), thereby obtaining the compound of formula I-1.

8. A method of synthesis of a hexabenzocoronene-based compound according to claim 6 of following formula I-1:

formula I-1

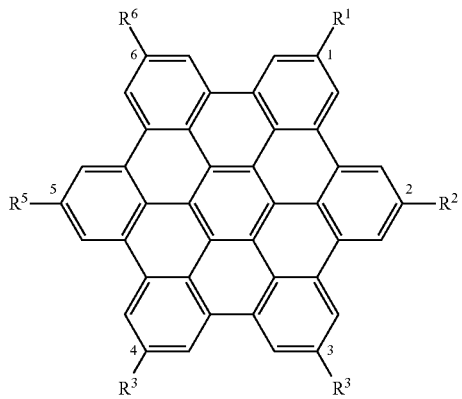

wherein $R^1$, $R^3$, $R^4$ and $R^6$ are identical and are a carboxylic group (—COOH), and $R^2$ and $R^5$ are identical and are chosen among a poly(3-oxypentylthiophene) (P3OPT) substituent and a poly(3-hexylthiophene) (P3HT), the method comprising the following steps:

a) reacting a compound of following formula (3):

formula (3)

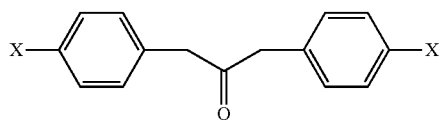

wherein X is a halogen chosen among Br, Cl and I with an equimolar amount of 1,2 phenylethan-1,2 dione (benzil), thereby obtaining a compound of following formula (4):

formula (4)

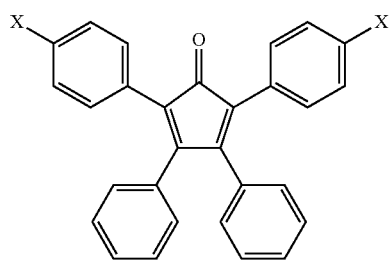

wherein X is as defined above, b) Diels-Alder reaction of the compound of formula (4) obtained in step a) with 1,2-bisphenylacetylene of following formula (4b):

formula (4b)

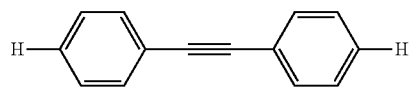

thereby obtaining a compound of following formula (5):

formula (5)

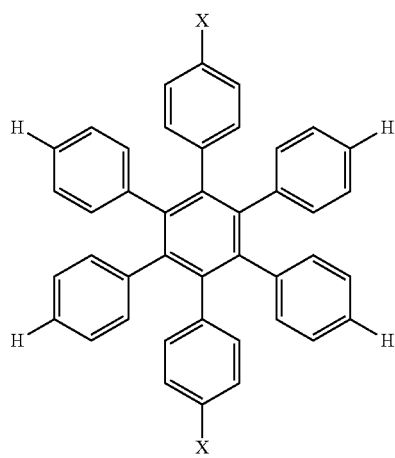

wherein X is as defined above, c) reacting of the compound of formula (5) obtained in step b) with a dioxaborolane derivative, thereby obtaining a compound of following formula (6):

formula (6)

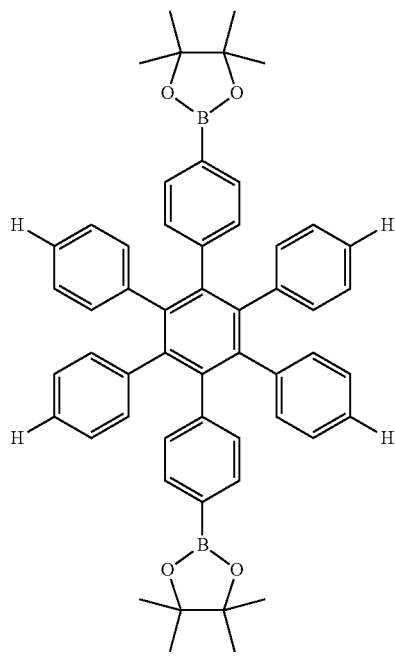

d1) Friedel-Crafts acylation between an acid chloride and the compound of formula (6) obtained in step c) and tert-butyl chloride using as catalyst $FeCl_3$, thereby obtaining a compound of following formula (6'):

formula (6')

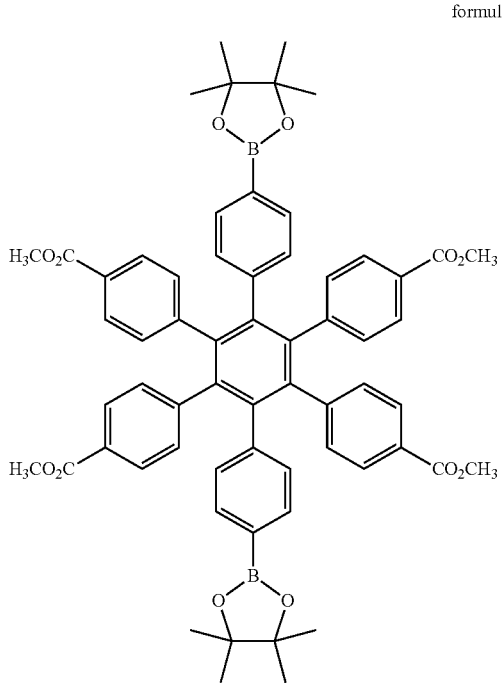

e1) Suzuki-Miyaura coupling of the compound of formula (6') obtained in step d1) with a polymer of following formula (1) or of a polymer of following formula (2):

formula (1)

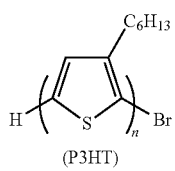

(P3HT)

wherein n is comprised between 4 and 80 formula (2)

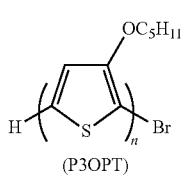

(P3OPT)

wherein n is comprised between 4 and 80 thereby obtaining a compound of following formula (7') when the polymer has the above formula (1):

formula (7')

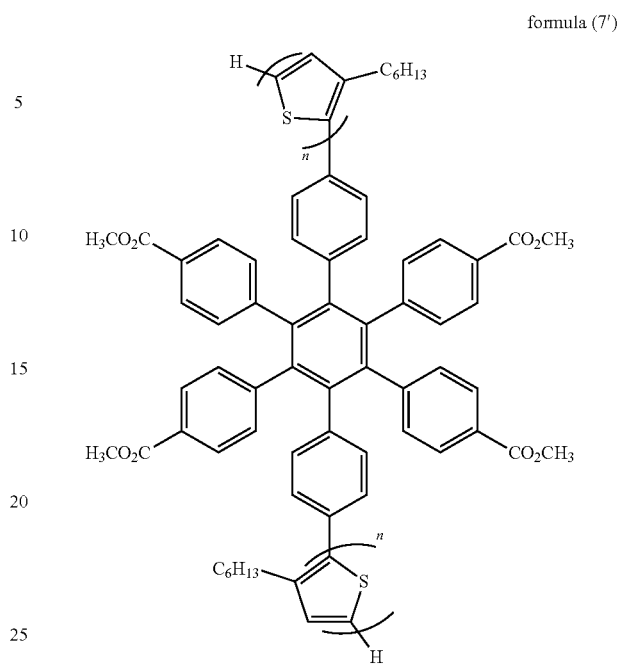

wherein n is comprised between 4 and 80 or a compound of following formula (8') when the polymer has the above formula (2):

formula (8')

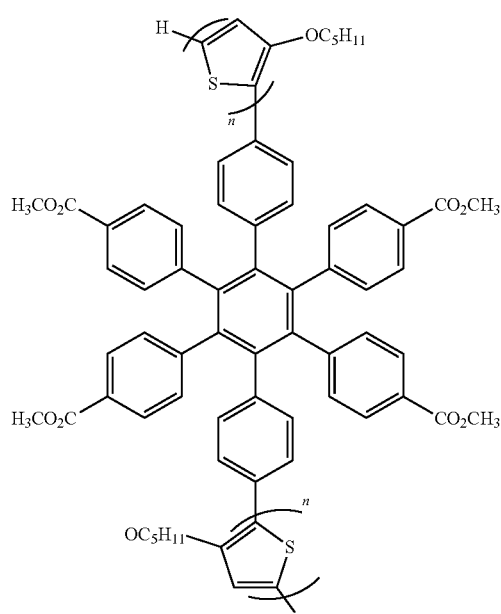

wherein n is comprised between 4 and 80 f) cyclodehydrogenation reaction of the compound of formula (7') or of the compound of formula (8'), thereby obtaining the compound of formula I-1.

9. The method according to claim 7, wherein step f) of cyclodehydrogenation of the compound of formula (9) or of the compound of formula (10) is carried out by reacting this compound with 2,3-dichloro-5,6-dicyano-1,4-benzoquinone (DDQ).

10. The method according to claim 7, wherein step f) is a step of reaction of the compound of formula (9) or the compound of formula (10) with FeCl₃, dissolved in CH₃NO₂.

11. A method of synthesis of a hexabenzocoronene-based compound according to claim 6 of following formula I-1:

formula I-1

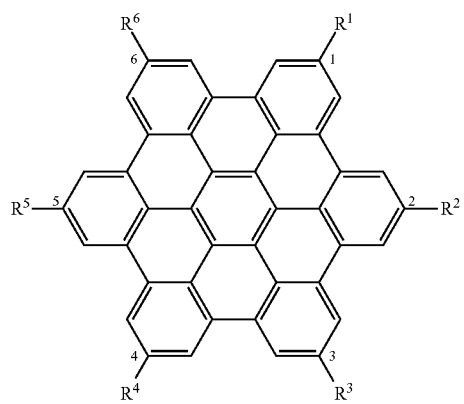

wherein R¹, R³, R⁴ and R⁶ are identical and are a carboxylic group (—COOH), and R¹ and R² are identical and are chosen among a poly(3-oxypentylthiophene) (P3OPT) substituent and a poly(3-hexylthiophene) (P3HT), the method comprising the following steps:

a) reaction of a compound of following formula (3):

formula (3)

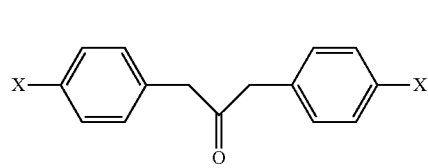

wherein X is a halogen chosen among Br, Cl and I with an equimolar amount of 1,2 phenylethan-1,2 dione (benzil), thereby obtaining a compound of following formula (4):

formula (4)

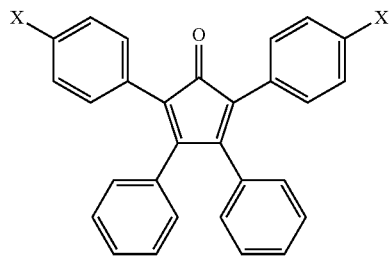

wherein X is as defined above, b) Diels-Alder reaction of the compound of formula (4) obtained in step a) with 1,2-bisphenylacetylene of following formula (4b):

formula (4b)

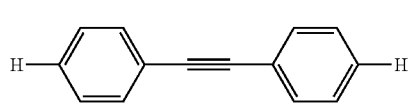

thereby obtaining a compound of following formula (5):

formula (5)

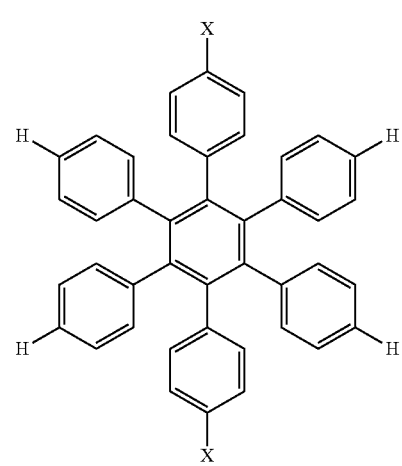

wherein X is as defined above, c) reaction of the compound of formula (5) obtained in step b) with a dioxaborolane derivative, thereby obtaining a compound of following formula (6):

formula (6)

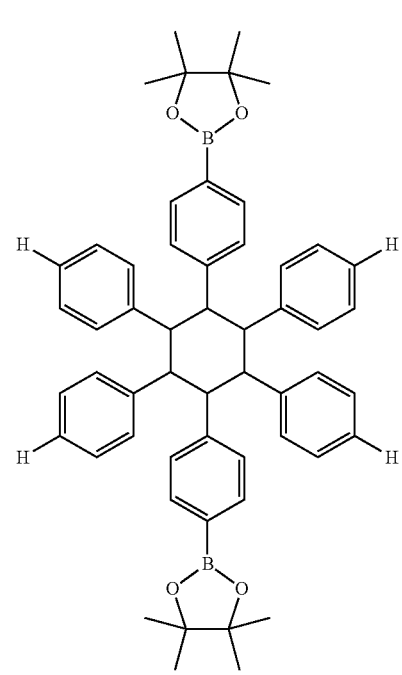

d) Suzuki-Miyaura coupling of the compound of formula (6) obtained in step c) with a polymer of following formula (1) or a polymer of following formula (2):

formula (1)

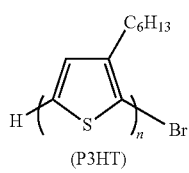

(P3HT)

wherein n is comprised between 4 and 80 formula (2)

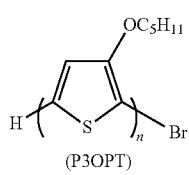

(P3OPT)

wherein n is comprised between 4 and 80
thereby obtaining a compound of following formula (7) when the polymer has the above formula (1):

formula (7)

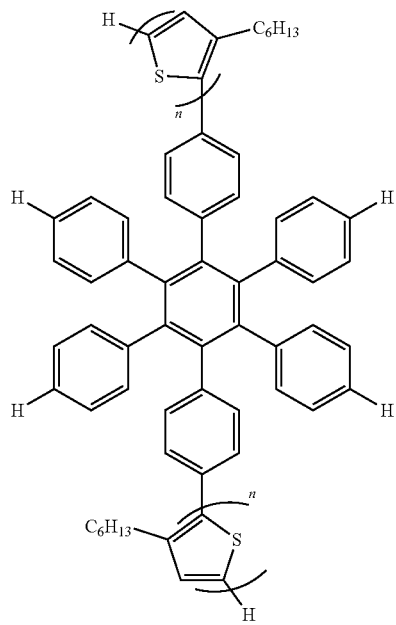

wherein n is comprised between 4 and 80
or a compound of following formula (8) when the polymer has the above formula (2):

formula (8)

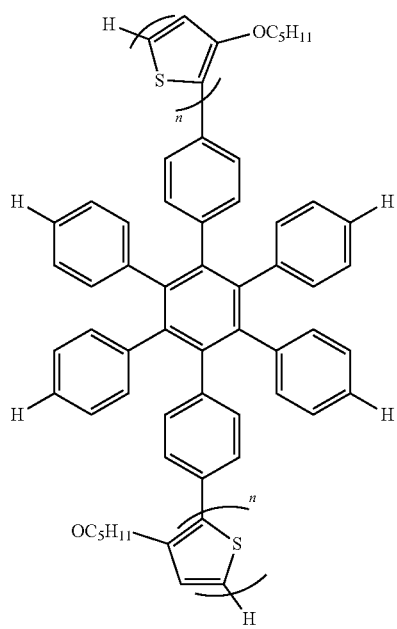

wherein n is comprised between 4 and 80 e2) cyclodehydrogenation of the compound of formula (7) or of the compound of formula (8) by reacting this compound with 2,3-dichloro-5,6-dicyano-1,4-benzoquinone (DDQ) or with $FeCl_3$ in $CH_3NO_2$, thereby obtaining the compound of following formula (13) when the polymer has the above formula (1):

formula (13)

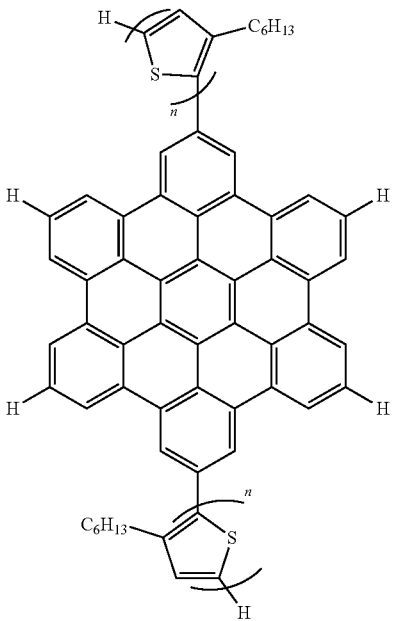

wherein n is comprised between 4 and 80
or a compound of following formula (14) when the polymer has the above formula (2):

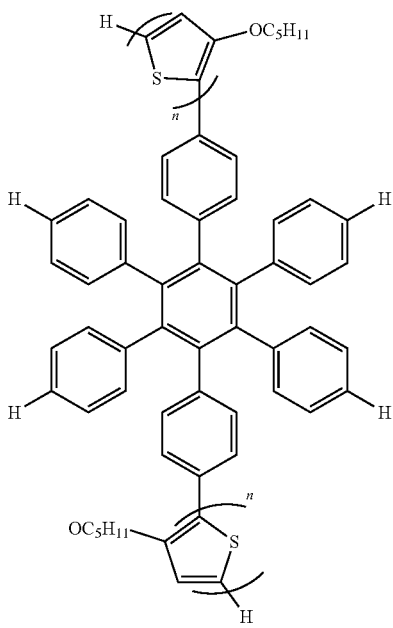

formula (14)

wherein n is comprised between 4 and 80 f1) Friedel-Crafts acylation between an acid chloride and the compound of formula (13) or the compound of formula (14), thereby obtaining the compound of formula I-1.

12. The method according to claim 7, wherein, in step c), the dioxaborolane derivative is 2-isopropoxy-4,4,5,5-tetramethyl-[1,3,2]dioxaborolane.

13. The method according to claim 8, wherein step b) is carried out in a microwave-heated apparatus at a temperature comprised between 200 and 256° C. and a power of between 250 and 350 W during between 60 minutes and 300 minutes.

14. The method according to claim 8, furthermore comprising a step g) of synthesis of the polymer of formula (1) (P3HT) or of the polymer of formula (2) (P3OPT).

15. The method according to claim 14, wherein step g) is a step of synthesis of the polymer of formula (1) (P3HT) by Grignard Metathesis (GRIM) polymerization of 2,5-dibromo-3-hexylthiophene or 2,5-diiodo-3-hexylthiophene or 2-bromo-5-iodo-3-hexylthiophene or 2-iodo-5-bromo-3-hexylthiophene.

16. The method according to claim 14, wherein step g) is a step of synthesis of polymer (2) (P3OPT) comprising the Grignard Metathesis (GRIM) polymerization of 2,5-dibromo(3-oxypentylthiophene) or 2,5-diiodo-(3-oxypentylthiophene) or 2-bromo-5-iodo-(3-oxypentylthiophene) or 2-iodo-5-bromo-(3-oxypentylthiophene).

17. A donor: acceptor layer comprising a stack of a hexabenzocoronene-based compound of following formula I:

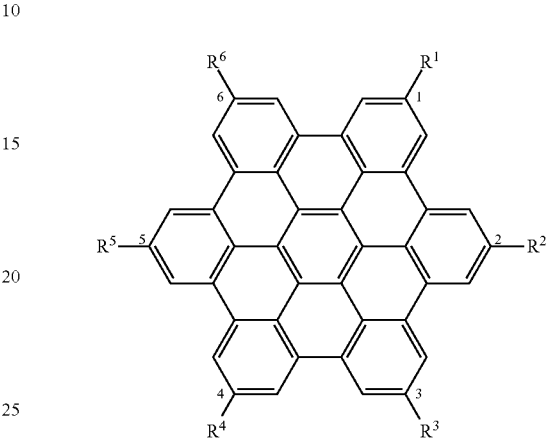

wherein $R^1$, $R^3$, $R^4$ and $R^6$ are independently from each other chosen among a carboxylic (—COOH) group, a cyano (—C≡N) group, an isocyano (—N$^+$≡C$^-$) group, a cyanate (—O—C≡N) group and a —F group, and $R^2$ and $R^5$ are, independently from each other, chosen among a poly(3-oxypentylthiophene) (P3OPT) substituent and a poly(3-hexylthiophene) (P3HT) substituent.

18. A device comprising at least one hexabenzocoronene-based compound according to claim 1.

19. The device of claim 18 which is a photovoltaic cell.

20. The method according to claim 8, wherein step f) of cyclodehydrogenation of the compound of formula (7') or of the compound of formula (8') is carried out by reacting this compound with 2,3-dichloro-5,6-dicyano-1,4-benzoquinone (DDQ).

21. The method according to claim 8, wherein step f) is a step of reaction of the compound of formula (7') or the compound of formula (8') with FeCl$_3$, dissolved in CH$_3$NO$_2$.

* * * * *